United States Patent
Nifantiev et al.

(10) Patent No.: US 6,777,402 B2
(45) Date of Patent: Aug. 17, 2004

(54) WATER-SOLUBLE PORPHYRIN DERIVATIVES FOR PHOTODYNAMIC THERAPY, THEIR USE AND MANUFACTURE

(75) Inventors: Nikolay E. Nifantiev, Moscow (RU); Dmitri V. Yashunsky, Moscow (RU)

(73) Assignee: CeramOptec Industries, Inc., East Longmeadow, MA (US)

( * ) Notice: Subject to any disclaimer, the term of this patent is extended or adjusted under 35 U.S.C. 154(b) by 15 days.

(21) Appl. No.: 10/151,764

(22) Filed: May 20, 2002

(65) Prior Publication Data

US 2003/0023081 A1 Jan. 30, 2003

Related U.S. Application Data

(63) Continuation-in-part of application No. 09/871,772, filed on Jun. 1, 2001, now abandoned.

(51) Int. Cl.[7] .................... C07D 487/22; A61K 31/409; A61P 35/00; A61P 33/00
(52) U.S. Cl. ........................ 514/183; 540/145; 514/410
(58) Field of Search .......................... 540/145; 514/183, 514/410

(56) References Cited

U.S. PATENT DOCUMENTS

| 5,330,741 A | 7/1994 | Smith et al. .................... 424/9 |
| 5,378,835 A | 1/1995 | Nakazato .................... 540/145 |

FOREIGN PATENT DOCUMENTS

RU 2144538 C1 1/2000

OTHER PUBLICATIONS

Lotjonen, S et al, "An improved Method for the Preparation of (10R)– and (10S)– Pheophytins a and b", Synthesis, p 705–708 (Sep. 1983).
Hynninen, P H et al, "Preparation of Phorbin Derivatives from Chlorophyll Mixture Utilizing the Principle of Selective Hydrolysis", Synthesis p 539–541 (Jul. 1980).
Lotjonen, S et al, "A Convenient Method for the Preparation of Chlorin e6 and Rhodin g7 Trimethyl Esters", Synthesis, p 541–543 (Jul. 1980).
Smith, K M et al, "Meso Substitution of Chloro–phyll Derivatives: Direct Route for Transform–action of Bacteriopheophorbides d into Bacterio pheophorbides c", J. Am. Chem. Soc., v 107, n 17, p 4946–4954 (1985).
Pandey, R K et al, "Chlorin and Porphyrin Derivatives As Potential Photosensitizers in Photodynamic Therapy", Photochem. and Photobiol., v 53, n 1, p 65–72 (1991).
Adams, K R et al, "Second Generation Tumour Photosensitizers: The Synthesis and Biological Activity of Octaalkyl Chlorins and Bacterio–chlorins with Graded Amphiphilic Character", J. Chem. Soc. Perkin Trans 1, p 1465–1470 (1992).
Pandey, R K et al, "Pinacol Pinacolone Rearrange–ments in vic–Dihydroxychlorins and Bacterio–chlorins: Effect of Substituents at the Peripheral Positions", J. Org. Chem., v 62, p 1463–1472 (1997).
Leach et al, "Effectiveness of a Lysyl Chlorin p6/Chlorin p6 Mixture in Photodynamic Therapy of the Subcutaneous 9L Glioma in the Rat", Cancer Research 52, 1235–1239, Mar. 1, 1992.
Rimington et al, "Hematoporphyrin Ethers—II. Improvements in Method, Synthesis of the Dihexyl, Dicyclohexanyl and Diphenyl Ethers and their Preliminary Biological Evaluation", Int. J. Biochem. V. 20, No. 10, 1139–1149, 1988.

Primary Examiner—Mark L Berch
Assistant Examiner—Kahsay Habte
(74) Attorney, Agent, or Firm—BJ Associates; Bolesh J. Skutnik; Thomas J. Ryan

(57) ABSTRACT

High purity pharmaceutical-grade water-soluble porphyrin derivatives given by formula 1 or 2 in the specification, and new methods to prepare and use such porphyrin derivatives are disclosed. A preferred method comprises the steps of one- or two-step direct acidic alcoholysis of biological raw material producing a crystalline alkyl pheophorbide, conversion of the obtained alkyl pheophorbide into an acidic porphyrin, and reaction of the acidic porphyrin in water or in an aqueous organic solution with a hydrophilic organic amine. Another preferred method comprises reaction of acidic porphyrins prepared in water or in aqueous organic solution with a hydrophilic organic amine. Another preferred method comprises the additional step of purification of the resultant water-soluble porphyrin derivative by reversed phase chromatography using volatile solvents. The disclosed compounds are useful as photosensitizers for the photodynamic therapy of cancer, infectious and other diseases as well as for light irradiation treatments in other cases.

31 Claims, 2 Drawing Sheets

WATER-SOLUBLE PORPHYRIN DERIVATIVES FOR PHOTODYNAMIC THERAPY, THEIR USE AND MANUFACTURE

REFERENCE TO RELATED CASE

This application is a continuation-in-part of U.S. patent application Ser. No. 09/871,772 filed on Jun. 1, 2001 now abandoned by Nikolay E. Nifantiev, inventor, entitled "WATER SOLUBLE PORPHYRIN DERIVATIVES AND METHODS OF THEIR PREPARATION", and incorporated by reference herein.

FIELD OF THE INVENTION

The invention relates to the chemistry of biologically active compounds, namely, to a new method to prepare water-soluble porphyrin derivatives, particularly chlorin, bacteriochlorin, pheophorbide and bacteriopheophorbide derivatives of types 1 and 2. The compounds of the present invention can be used as photosensitizers for the photodynamic therapy of cancer, infections and other diseases as well as for light irradiation treatments in other cases.

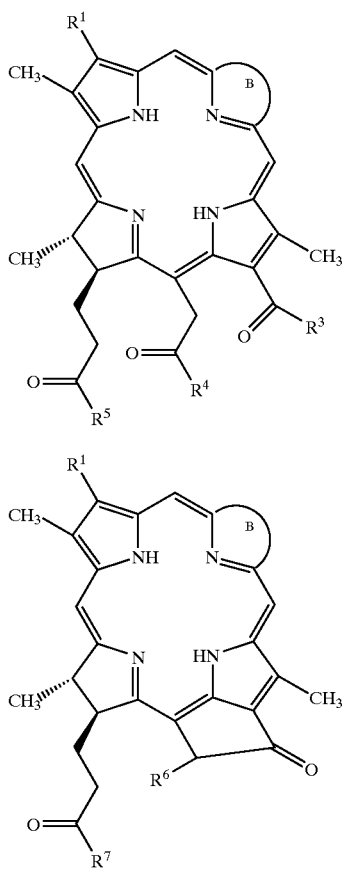

Wherein B is a ring having the structure:

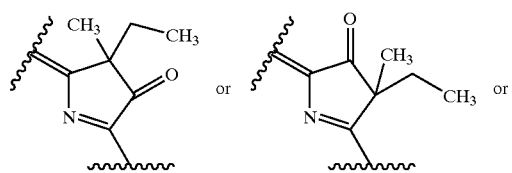

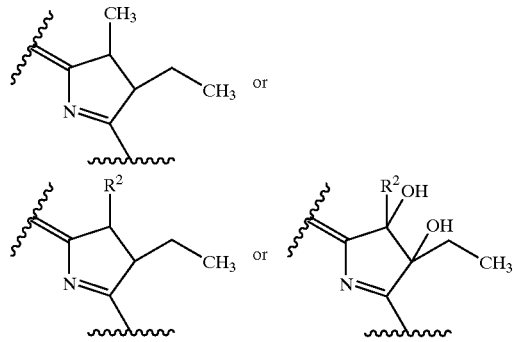

Wherein:

$R^1$=—CH=CH$_2$, —CH(OAlk)CH$_3$, —CHO, —C(O)CH$_3$, —CH$_2$CH$_3$, —CH(Alk)CH(COAlk)$_2$, —CH$_2$CH(COAlk)$_2$, —CH(Alk)CH$_2$COAlk, —CH(Alk)CH$_2$CH(OH)CH$_3$, and —CH$_2$CH$_2$CH(OH)CH$_3$ $R^2$=—CH$_3$, —CHO, —CH(OH)Alk, —CH=CHAlk, CH$_2$OH, and CH$_2$OAlk;

$R^3$=—OH, —OAlk, —NH-Alk, NH—X—COO$^-$(HG)$^+$, —NH—Y—NR$^8$R$^9$, -and NH—Y—OH;

$R^4$=—OAlk, —NH-Alk, and NH—X—COO$^-$(HG)$^+$;

$R^5$=—OAlk, —NH-Alk, and NH—X—COO$^-$(HG)$^+$;

$R^6$=H and —COOAlk;

$R^7$=—O$^-$(HG)$^+$, —OAlk, —NH-Alk, and —NH—X—COO$^-$(HG)$^+$;

$R^8$=H and Alk $R^9$=H and Alk

Wherein:

—NH—X—COO$^-$=the residue of organic amino acid;

X=alkylidene, peptides, oligopeptides and —(CH$_2$CH$_2$O)$_n$CH$_2$CH$_2$—, wherein n=1–30;

Y=alkylidene and —(CH$_2$CH$_2$O)$_n$CH$_2$CH$_2$—, wherein n=1–30;

G=a hydrophilic organic amine (f.ex. N-methyl-D-glucamine and other amino-group containing carbohydrate derivatives, TRIS, amino acids, oligopeptides); and Alk=an alkyl substituent.

BACKGROUND OF THE INVENTION

Photodynamic therapy (PDT) is one of the most promising new techniques now being explored for use in a variety of medical applications (Photodynamic therapy, basic principles and clinical applications. Eds. B. W. Henderson, Th. J. Dougherty, Marcel Dekker, 1992, New York), and particularly is a well-recognized treatment for the destruction of tumors (Photodynamic tumor therapy. 2$^{nd}$ and 3$^{rd}$ generation photosensitizers. Ed. J. G. Moser, Harwood Academic Publishers, 1998, Amsterdam). Porphyrins are compounds widely used in PDT. A major problem in the pharmaceutical application of porphyrins is their low solubility in physiological solutions. This renders it nearly impossible to prepare effective pharmaceutical grade injectable solutions for PDT and other applications.

Methods to prepare water soluble porphyrin derivatives for PDT are known in the art. U.S. Pat. No. 5,330,741 by Smith et al discloses a method to prepare trisodium lysyl-chlorin p$_6$ involving the reaction between purpurin 18 methyl ester, resulting from methyl pheophorbide a transformation, and aqueous lysine in methylene chloride in the presence of pyridine. The mixture is stirred at room temperature for 12 hours, followed by the removal of the solvents in a high vacuum. The so prepared crude product is purified by reversed-phase HPLC and subsequently lyophilized. To prepare an injectable solution for the PDT of cancer, the preparation is first dissolved in phosphate buffer solution and then 0.1 N sodium hydroxide is added The pH value of the solution is adjusted to pH 7.35 using 0.1 N HCl followed by sterility filtration through a microporous filter.

Drawbacks of the above mentioned method include a lack of reproducibility and difficulty in the work-up and utilization of toxic reagents, which make it hardly appropriate for pharmaceutical manufacturing. Additionally, the prepared water soluble product of interest is stable in an aqueous solution for only 24 hours at 4° C. in the dark, and in solid form for up to 4 months at 4° C. in the dark [M. W. Leach, R. J. Higgins, J. E. Boggan, S.-J. Lee, S. Autry, K. M. Smith, Effectiveness of a Lysylchlorin $p_6$/Chlorin $p_6$ mixture in Photodynamic Therapy of the Subcutaneous 9L Glioma in the Rat. Cancer Res., 1992, 52, 1235–1239; U.S. Pat. No. 5,330,741].

There is a method to prepare a water-soluble sodium salt of pheophorbide a (3), described in U.S. Pat. No. 5,378,835 by Nakazato. According to this invention, pheophorbide a (4) is dissolved in diethyl ether, and a very diluted solution of alkali in n-propanol, iso-propanol or in their mixture is added dropwise and very slowly to the solution. The reaction is maintained up to the complete precipitation of pheophorbide a salt, which is separated by centrifugation and dried in vacuo. Then the product is dissolved in water resulting in a solution with concentration 0.5% and pH 9.2–9.5 that is then diluted with a phosphate buffer with pH 7.4–7.8.

The drawback of the method described by Nakazato is the fact that a concentrated (>1%) injectable pheophorbide a solution in water can not be generated by this technique. Additionally, the authors of the present invention demonstrated the chemical instability of such salts when stored dry, and their incomplete ability to dissolve in water after having been stored in the dry state.

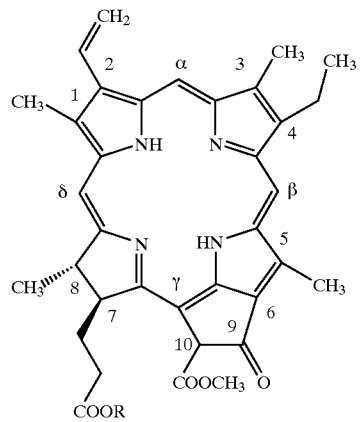

(3) R = Na
(4) R = H
(5) R = Me
(6) R = Et

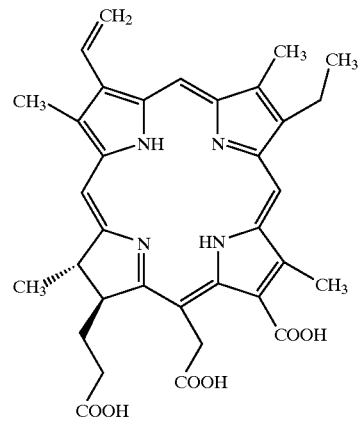

The closest analogue to the present invention is the method disclosed in Russian Patent No. RU2144538 by G. V. Ponomarev et al to prepare water-soluble complexes of chlorin $e_6$ (7) with spacious organic amines including N-methyl-D-glucosamine by a multi-step straightforward sequence of chemical reactions including preparation of chlorophyll a from *Spirulina Platensis* cyanobacteria biomass, further conversion into chlorin $e_6$ according to standard procedures [S. Lötjönen, P. H. Hynninen, An improved method for the preparation of (10R)- and (10S)-pheophytins a and b. Synthesis. 1983, 705–708; P. H. Hynninen, S. Lötjönen, Preparation of phorbin derivatives from chlorophyll mixture utilizing the principle of selective hydrolysis. Synthesis. 1980, 539–541; S. Lötjönen, P. H. Hynninen, A convenient method for the preparation of wet chlorin $e_6$ and rhodin $g_7$ trimethyl esters. Synthesis, 1980, 541–543] with an overall yield exceeding 50% after precipitation of chlorin $e_6$ by way of stepwise addition of water to its acetone solution, followed by separation by centrifugation and 3-fold washing with water and subsequent treatment of wet chlorin $e_6$ with water solution of 2 g-eq. spacious organic amine.

The key disadvantages of this method, which cause critical difficulties for preparative syntheses of water-soluble chlorins and particularly for industrial syntheses and drug manufacturing, are the following:

1. Chlorin $e_6$ as an intermediate product is obtained as a wet mass with unknown definite content of chlorin $e_6$. This instability of the amount of chlorin e6 obtained creates uncertainties that undermine the ability to standardize further resultant solutions.

2. The key intermediate in the synthetic sequence is pheophorbide a (4) which is difficult to handle for purification and standardization due to its acidic properties. Separation of pheophorbide a (4) via repeatable precipitations (as used by Ponomarev) is not quantitative and thus not convenient for large scale preparations.

3. Pheophorbide a (4) obtained by the indicated method contains impurities that are difficult to separate. This disadvantage causes uncertainty in the quantification of pheophorbide a (4) and disturbs the chemical opening of cyclopentanon ring in the course of transformation of pheophorbide a (4) into chlorins.

4. It should be noted that the samples of water soluble salts of chlorin $e_6$ being prepared according to Ponomarev contain a variety of impurities of non-porphyrin and porphyrin types which could not be separated from the target chlorin $e_6$ product with the use of the procedures described therein. Particularly, among the porphyrin impurities one could note by using TLC and HPLC methods are pheophorbide a (4), purpurin 18 (8), chlorin p6 (9) and some other concomitants.

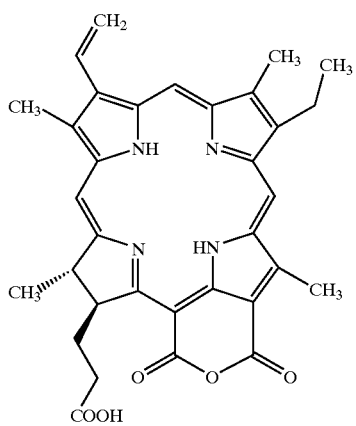

(8)

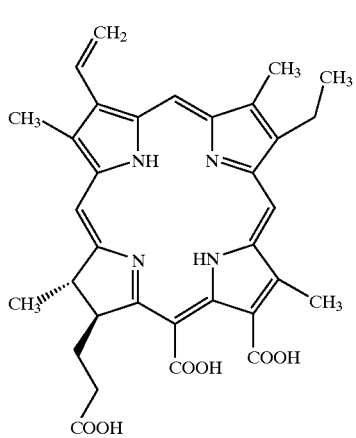

(9)

It could be noted that the compounds of types (4), (8) and (9) as salts with hydrophilic amines of the above invention are characterized by remarkably lower water solubility as compared with their respective chlorin $e_6$ salts. Nevertheless in the presence of chlorin $e_6$ salts the compounds of types (4), (8) and (9) as salts with hydrophilic amines of the above invention are much more water soluble than probably could be explained by possible formation of complexes with chlorin $e_6$ salts. This phenomenon makes it impossible to separate the chlorin $e_6$ products from impurities like the compounds of types (4), (8) and (9) by using their different water solubility.

5. The organic amines being used by Ponomarev for preparation of water-soluble chlorins are not optimal for practical applications. Particularly D-glucosamine, which forms complexes with chlorin bearing a higher solubility, is not stable enough due to possible oxidation at its aldehyde group. At the same time D-glucosamine can be present in the solution in several isomeric forms that brings structural uncertainties and therefore respective difficulties for detailed structural characterization thus failing to meet the demand of quality control for pharmaceutical preparations. One more spacious amine is used by Ponomarev, namely N-methyl-D-glucosamine, which has the same disadvantages as the above mentioned D-glucosamine and is moreover not readily available due to its difficult preparation.

6. Ponomarev claims the formation of water-soluble salts of chlorin $e_6$ derivatives with spacious organic amines which is very uncertain because usual spacious organic amines, e.g. that ones containing tert-butyl, neopentyl, adamantyl, cyclohexyl groups, could not be used in the preparation of water-soluble chlorin $e_6$ salts due to high hydrophobicity of spacious organic moieties.

This aspect along with other aspects mentioned above make use of the method claimed by Ponomarev impossible for manufacturing of effective pharmaceutical grade compositions according to GMP standards.

Starting porphyrin derivatives for the syntheses of interest in the present invention are traditionally obtained from pure and standard raw porphyrin materials methyl (5) or ethyl (6) pheophorbide a. General methods known to date for the separation of porphyrins from biological raw materials consist of a long sequence of laborious washings with organic solvents and/or freezing steps to destroy cell walls of the biomaterial, and repeatable extractions together with chemical treatments of the biomass to first obtain chlorophyll, which is then transformed into pheophytin and subsequently hydrolyzed to yield pheophorbide (K. M. Smith, D. A. Goff and D. J. Simpson, *J. Amer. Chem. Soc.*, 1985, 107, 4946–4954; R. K. Pandey, D. A. Bellnier, K. M. Smith and T. J. Dougherty, *Photochem. Photobiol.*, 1991, 53, 65–72; W. A. Svec, In: The porphyrins, ed. D. Dolphyn, NY, Academic Press, 1978, 5, 342–400).

Thus, there is a need to provide an easy and efficient method for the preparation of pure and chemically stable water-soluble pharmaceutical grade porphyrin derivatives with standard content of the desired substance, suitable for medical applications especially in photodynamic therapy. The present invention fulfills this need and further provides other related advantages.

OBJECTIVES AND BRIEF SUMMARY OF THE INVENTION

It is an object of the present invention to provide chemically stable water-soluble porphyrin derivatives with a standard content of the desired substance and suitable for various medical applications, particularly for PDT.

It is another object of the present invention to provide pharmaceutical grade high-purity water-soluble porphyrin derivatives that are effective in pharmaceutical compositions.

It is another object of the present invention to provide a method to prepare chemically stable water-soluble porphyrin derivatives.

It is yet another object of the present invention to provide an easy and time-efficient method to prepare chemically stable water-soluble porphyrin derivatives from biological raw materials while avoiding the disadvantages of the prior art.

It is still another object of the present invention to provide chemically stable water-soluble porphyrin derivatives in a pharmaceutically acceptable preparation for use in medical applications such as treatment of cancer and other hyperproliferative diseases, infections and others.

An embodiment of the present invention consists of a method to prepare water-soluble porphyrin derivatives comprising the steps of one- or two-step direct acidic alcoholysis of biological raw material producing a crystalline alkyl pheophorbide, conversion of the obtained alkyl pheophorbide into an acidic porphyrin, and reaction of the acidic porphyrin in water or in an aqueous organic solution with a hydrophilic organic amine.

Another embodiment of the present invention consists of a method to prepare water-soluble porphyrin derivatives, comprising reaction of the acidic porphyrin in water or in aqueous organic solution with a hydrophilic organic amine.

Yet another embodiment of the present invention consists of a method to prepare water-soluble porphyrin derivatives, comprising the steps of one- or two-step direct acidic alcoholysis of biological raw material producing crystalline alkyl pheophorbide, conversion of the obtained alkyl pheophorbide into an acidic porphyrin, reaction of the acidic porphyrin in water or in aqueous organic solution with a hydrophilic organic amine, and purification of the resultant water-soluble porphyrin derivative by reversed phase chromatography using volatile solvents.

In still another embodiment, the present invention provides a method to prepare water-soluble porphyrin derivatives comprising reaction of the acidic porphyrin in water or in aqueous organic solution with a hydrophilic organic amine, and purification of a water-soluble porphyrin derivative by reversed phase chromatography with the use of volatile solvents. Furthermore, the present invention provides a water-soluble porphyrin derivative of formulae (1) and (2), useful for pharmaceutical compositions for use in photodynamic therapy and other medical applications, obtained by the methods provided by the invention.

DETAILED DESCRIPTION OF THE PREFERRED EMBODIMENTS

Figure 1:
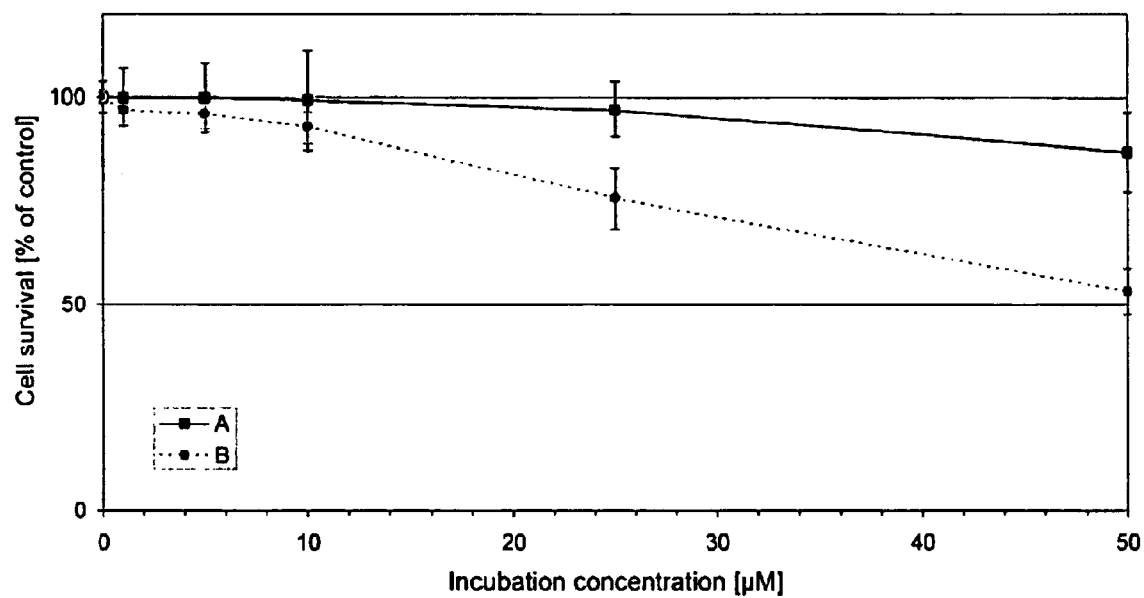
FIG. 1: Determination of dark toxicity (cytotoxicity, Example 14) of water-soluble salt of chlorin $e_6$ (7) with N-methyl-D-glucamine (10) being prepared (A) according to this invention (Example 9) and (B) according to Ponomarev (RU2144538); the test was performed in OV2774 cells under addition of different concentrations of the photosensitizer as indicated.
Figure 1:
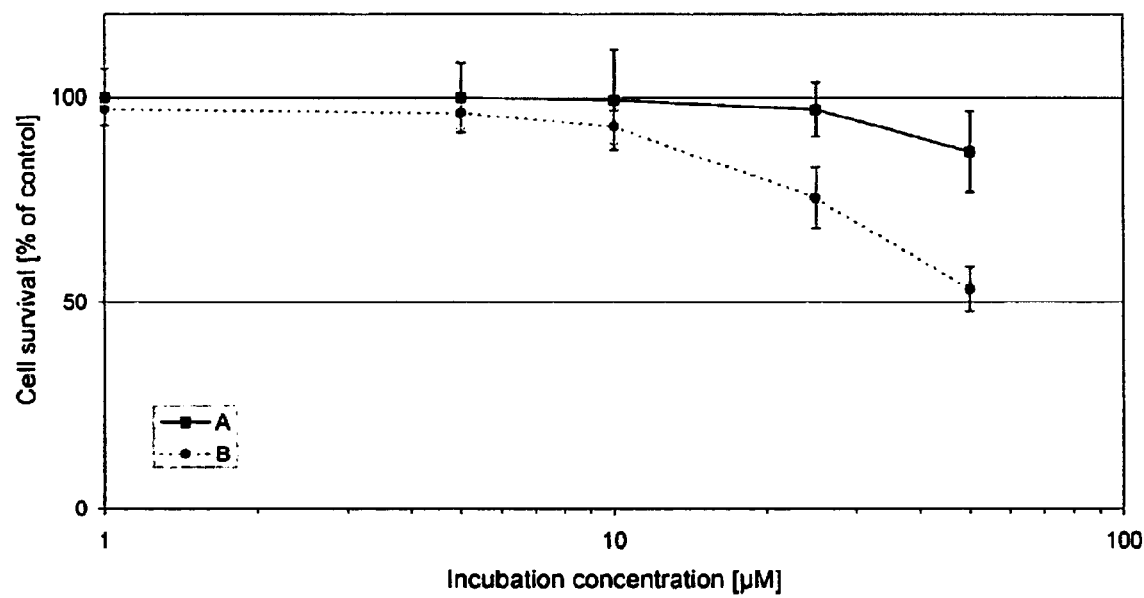

Prior to describing the invention, it may be helpful to set forth definitions of certain terms to be used within the disclosure.

Porphyrins are macrocyclic compounds with bridges of one carbon atom or one nitrogen atom respectively, joining pyrroles to form a characteristic tetrapyrrole ring structure. There are many different classes of porphyrin derivatives including those containing dihydro-pyrrole units. The term porphyrins will be used herein to refer to porphyrins, phtalocyanines, chlorins, pheophorbides, metallo derivatives thereof and other porphyrin-like compounds suitable for PDT and pharmaceutical preparations.

As used herein, biological raw materials are materials for preparation of compounds of the present invention, comprising e.g. plants, algae, blood components and insect excretions.

The aim of the present invention is achieved by the described method, comprising the reaction of acidic porphyrins in water or in an aqueous organic solution with a hydrophilic organic amine preferably with N-methyl-D-glucamine (10), which is a polyhydroxylated stable and non-toxic compound useful for drug preparation or with aminoalkyl and aminoaryl glycosides such as maltose derivatives (11) and (12) or other amino-groups bonded to carbohydrate derivatives. Other proposed reagents include, but are not limited to, tris(hydroxymethyl)aminomethane (also known as TRIS) (13), which is also a stable and non-toxic compound useful for drug preparation, or with TRIS derivatives such as compounds (14) and (15), as well as other types of hydrophilic amines such as bis(2-hydroxyethyl)amine (16). Amino acids or oligopeptides such as oligolysines, preferentially penta- and hexalysines, also can be used as hydrophilic organic amines suitable for preparation of water-soluble porphyrin derivatives according to the present invention.

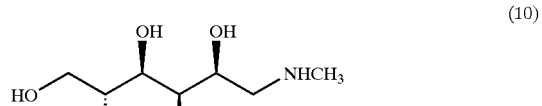

(10)

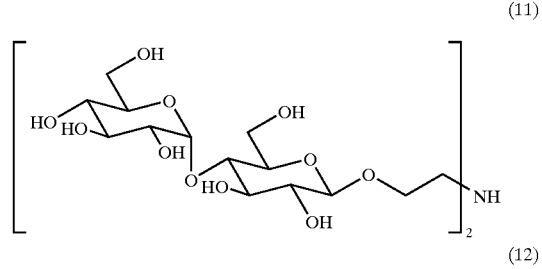

(11)

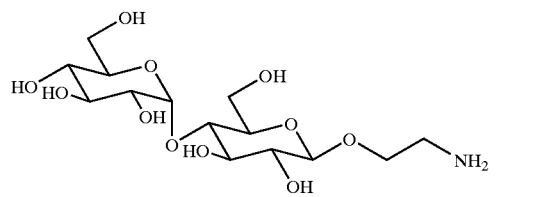

(12)

(13)

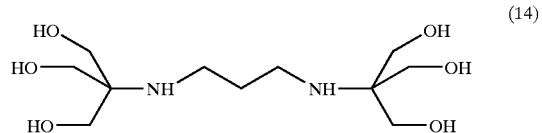

(14)

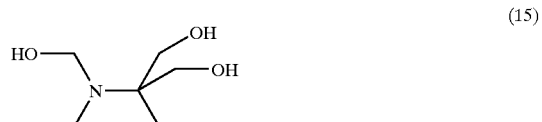

(15)

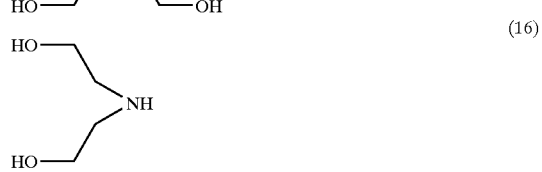

(16)

According to a preferred embodiment of the present invention, as described in Example 9, the quantitative stoichiometric reaction of chemically pure porphyrin (as free acid) and an appropriate hydrophilic organic amine is performed at room temperature under inert gas and in darkness. The solvent used is either chemically pure water which is degassed with inert gas (e.g. argon, helium or others), or if necessary a mixture of water with a suitable chemically pure and degassed organic solvent. The organic solvent is subsequently evaporated in vacuo without heating (to avoid possible destruction of starting porphyrin), and the product is freeze-dried. In some cases it is necessary to add an organic solvent to assist the reaction by dissolving the starting porphyrin so that the reaction of the porphyrin (as free acid) and appropriate hydrophilic organic amine takes place. Examples for possible organic solvents are acetone or a mixture of methylene chloride and methanol. The resulting freeze-dried water-soluble porphyrin is chemically pure and does not need any further purification except sterilization for medical or biological applications.

According to another preferred embodiment of the present invention, non pure ingredients can be used including wet pastes of starting porphyrins. The reaction is performed similarly as described above, but an excess amount of hydrophilic organic amine is used to react with all porphyrin components. After the concentration of reaction mixture in vacuo, the resulting water-soluble porphyrin is purified by chromatography on a column with appropriate reversed phase adsorbent, preferentially of RP C-8 or C-18 types. Fractions with target products are collected, evaporated in vacuo without heating to remove organic solvent, then freeze-dried to give the desired water-soluble porphyrin derivative. Protocols were developed for purification of water-soluble porphyrin derivatives by reversed phase chromatography with the use of volatile solvents results in products of a standard high quality that is critical for producing medical preparations.

Yet another embodiment of the present invention is an easy and efficient method of obtaining of porphyrin compounds from biological raw materials. The method comprises undergoing one- or two-step direct acidic alcoholysis of biological raw materials, preferably methanolysis or ethanolysis, giving crystalline alkyl pheophorbides (preferably methyl and ethyl) as key intermediate products suitable for a variety of further chemical transformations to obtain the target porphyrin derivatives. This simple and relatively fast procedure permits the preparation of porphyrin derivatives from biological raw materials without the use of laborious washings with organic solvents or freezing (to destroy cell walls) of the starting biomaterials and repeatable extractions required in previously known procedures.

Employing crystalline alkyl pheophorbides (preferably methyl and ethyl) as synthetic intermediate products provides the possibility of simple purification and standardization that is critical for producing pharmaceutical preparations for use in medical procedures such as PDT.

Performance of alcoholysis depends on the quality of starting biological raw material and particularly its dryness, which is important for maintaining the necessary acid concentration during alcoholysis. Thus, in the case of sufficiently dry material, e.g. dried Spirulina or Chlorella biomasses or powdered dry nettle leaves (see Examples 1–5) it is possible to perform direct one-step preparation of alkyl pheophorbides.

In the case of insufficiently dry raw material, the preparation of alkyl pheophorbides is performed by a two step alcoholysis as exemplified by the preparation of methyl pheophorbides a (5) and b (17) from spinach (see Example 6). In such cases the presence of too large an amount of water in the starting raw material prevents the development of an appropriate concentration of acid suitable to cleave the phytol ester. Nevertheless, pheophytins obtained after the first alcoholysis step are dry enough to be used in the preparation of crystalline alkyl pheophorbides within a second alcoholysis step.

Preparation of acidic porphyrins suitable for further transformation into water-soluble forms is performed by chemical transformation of porphyrin raw materials, for example crystalline alkyl pheophorbides, obtained from biological raw materials according to the procedure described in the present invention.

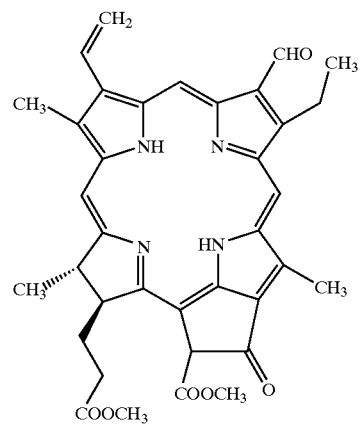

(17)

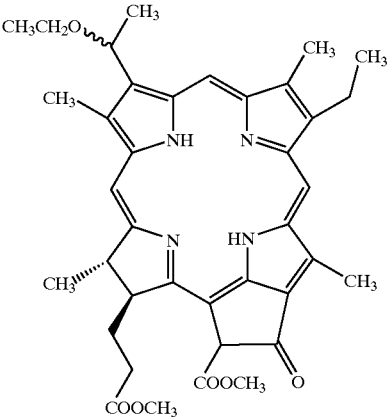

(18)

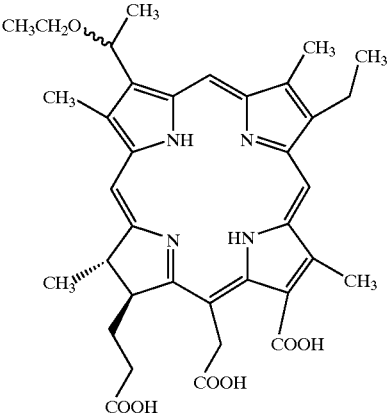

(19)

In particular, 2-devinyl-2-(1-alkoxyethyl)-chlorins $e_6$ such as ethoxy-derivative (19) can be obtained by hydrobromination of methyl or ethyl pheophorbides a with a saturated solution of HBr in acetic acid to produce respective 2-devinyl-2-(1-bromoethyl)-pheophorbides a, with further alcoholysis resulting in 2-devinyl-2-(1-alkoxyethyl)-pheophorbides a (e.g. compound 18) (C. Rimington, A. Roennestad, A. Western, and J. Moan, *Int. J. Biochem.*, 1988, 20, 1139–1149; K. R. Adams, C. R. Berembaum, R. Bonnett, A. N. Nizhnik, A. Salgado, and M. A. Valles, *J. Chem. Soc. Perkin Trans.* 1, 1992, 1465–1470) and subsequent saponification with formation of respective 2-devinyl-2-(1-alkoxyethyl)-chlorins $e_6$ as triacids (19) or water-soluble salts, e.g. with N-methyl-D-glucamine (10) (Example 10).

In a similar manner the reaction of other types of nucleophiles with 2-devinyl-2-(1-bromoethyl)-pheophorbides instead of their alcoholysis affords the formation of a variety of possible porphyrin derivatives to be used in the preparation of their water-soluble forms according to the present invention.

The method of the present invention for the preparation of water-soluble forms of different chlorin and pheophorbide derivatives can be also illustrated by Examples 15–30 (provided below) for the preparation of water-soluble salts of acids (4) and (20)–(33) with amine (10).

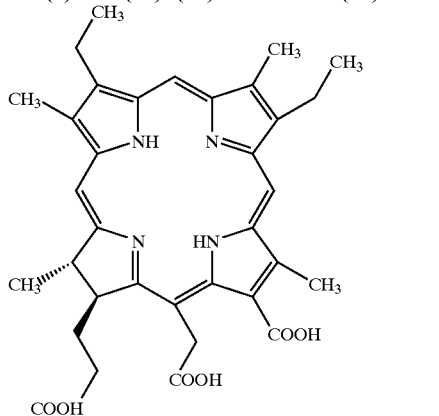

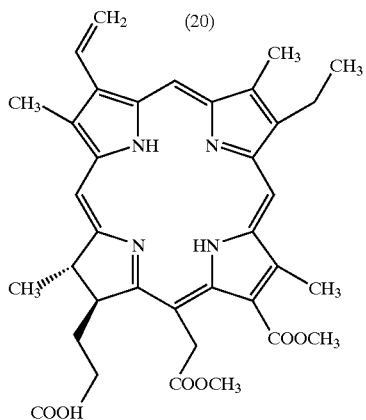
(20)

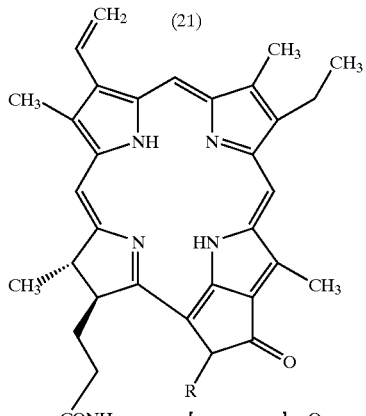
(21)

(22) R = COOMe
(23) R = H

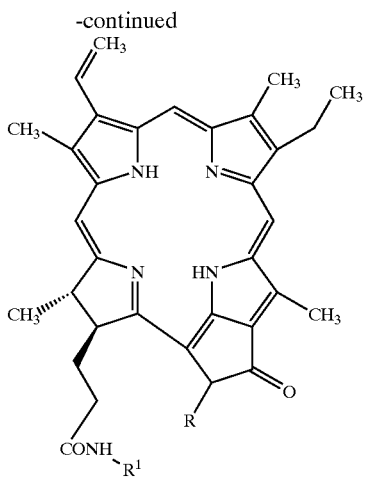

(24) $R^1 = CH_2CH_2(OCH_2CH_2)_2OCH_2COOH$, $R^2 = COOMe$
(25) $R^1 = CH_2CH_2(OCH_2CH_2)_2OCH_2COOH$, $R^2 = H$
(26) $R^1 = CH_2CH_2(OCH_2CH_2)_5OCH_2COOH$, $R^2 = H$
(27) $R^1 = CH_2COOH$, $R^2 = H$
(28) $R^1 = (CH_2)_5COOH$, $R^2 = H$

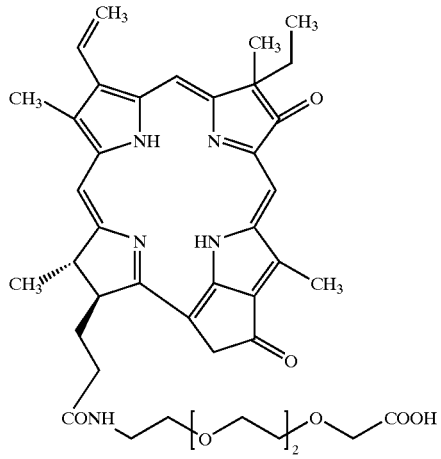

(29)

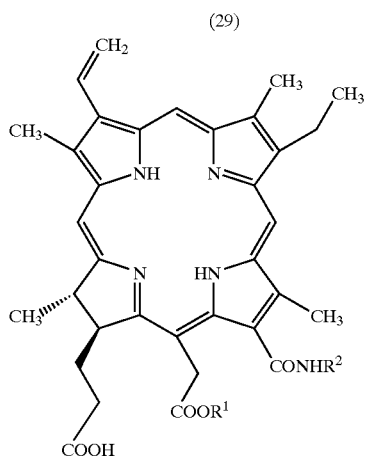

(30) $R^1 = H$, $R^2 = (CH_2)_3N(CH_3)_2$
(31) $R^1 = H$, $R^2 = (CH_2)_7NH_2$
(32) $R^1 = OCH_3$, $R^2 = (CH_2)_5COOH$
(33) $R^1 = OCH_3$, $R^2 = (CH_2)_2OH$

The reaction of acidic porphyrin derivatives with hydrophilic amines according to the present invention leads to the formation of respective water-soluble salts. Particularly in the case of pheophorbide derivatives these are monosalts, while bis-salts are formed from triacid chlorins (34) [via the intermediate formation of one of possible mono-salts, such as the intermediate (35), as shown in the Scheme 1] because the carboxyl group at position 6 (atom numbering is shown for compounds 4–6) does not exhibit sufficient acidity for salt formation.

To prevent such undesirable processes and to maintain clear and homogeneous solutions that are strictly necessary for the use of these solutions in medical applications like PDT, it is preferential to dissolve bis-salts in water in the presence of small and known amounts of the respective hydrophilic amine (e.g. lower than 2 mole equivalents, more Scheme 1

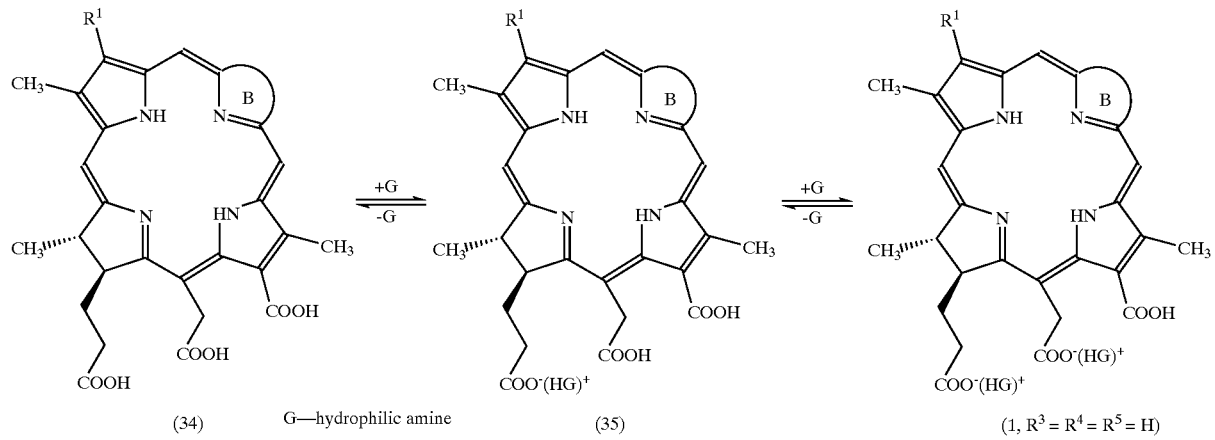

Because the water-soluble porphyrin salts of the present invention can be subjected to hydrolysis while dissolved in water (as exemplified for chlorins in Scheme 2), it is desirable to prepare the water-soluble salts of the present invention and store them in a dissolved state in the presence of the excess hydrophilic amine.

Water-soluble chlorin bis-salts of the present invention can be obtained in the individual state by column chromatography purification as exemplified in Example 9B. The dissolving in water of purified bis-salts is accompanied by the reversible hydrolysis to give mono-salts (e.g. of type 35, see Scheme 2) which may have reduced water solubility compared to bis-salts and probably even the parent chlorin (1) that is poorly soluble in water. Such processes can result in the formation of small amounts of precipitate during the storage of solutions.

preferably between 0.05 and 0.5 equivalents), so that the desired porphyrin derivatives are kept in the form of bis-salts and thus the formation of mono-salts and parent chlorins by hydrolysis of bis-salts is prevented.

The salts of chlorin and pheophorbide derivatives with hydrophilic amines, disclosed herein, have a water solubility on the order of tenths of one mg/L what makes them useful in a variety of applications. An additional object of the present invention is to prepare pheophorbide derivatives that carry an (one or more?) amino acid unit attached via peptide bond to form the salts with hydrophilic amines which are characterised by more than 100 times higher water-solubility than the parent pheophorbide compounds without amino acid fragments. Particularly, the salt of pheophorbide derivative (36) with N-methyl-D-glucamine (10) has a solubility of 40 mg/L while the derivatives (7, 20–33) carrying peptide Scheme 2

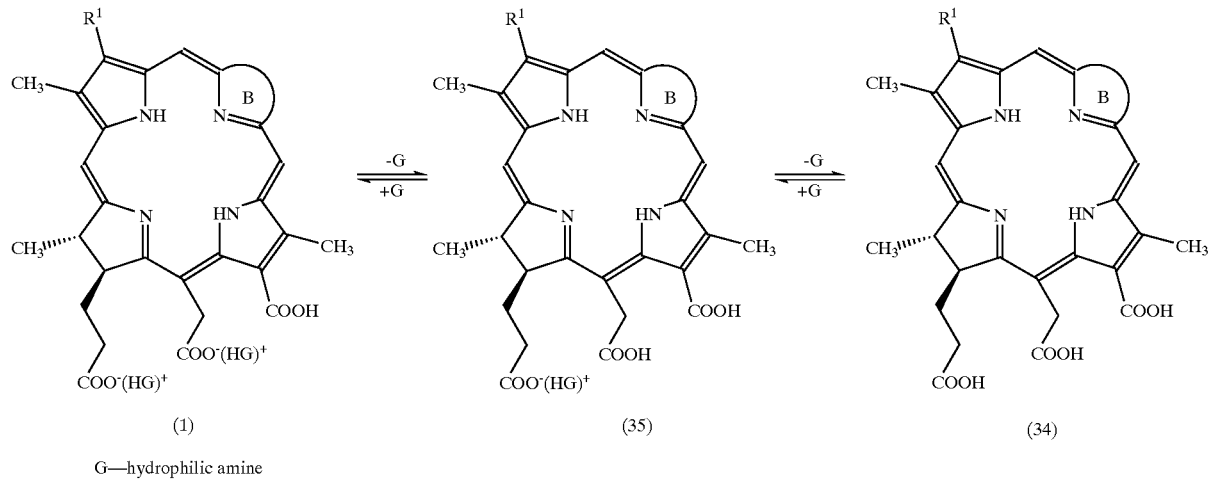

bond connected amino acid residues have a solubility greater than 5 g/L.

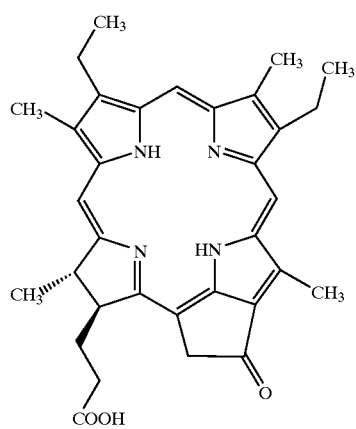

(36)

It is another object of the present invention to use the chemically stable and water-soluble porphyrin derivatives according to formulae (1) and (2) for various medical applications. Said compounds are especially preferable for use in PDT to treat cancer and other hyperproliferative diseases, infections, psoriasis, atherosclerosis, AMD, and other diseases and infections suitable for treatment with photodynamic therapy. Due to the water-solubility said compounds can be prepared in various pharmaceutically acceptable and active preparations for different administration methods, e.g. injections.

The present invention also provides for the use of high purity water-soluble porphyrin derivatives produced according to the present invention for photodynamic therapy of cancer and other hyperproliferative diseases and infections. PDT is accomplished by first incorporating the derivatives into a pharmaceutically acceptable application vehicle for delivery of the derivatives to a specific treatment site. In one embodiment, for diseases such as skin cancer or other dermatological diseases, the application vehicle is generally a dermatological cream, a gel or sometimes an aerosol liquid dispersant. After administering the derivatives in the vehicle to a treatment area, sufficient time is allowed so that the porphyrin derivatives preferentially accumulate in the diseased tissue. Lastly, the treatment area is irradiated with light of a proper wavelength and sufficient power to activate the porphyrin derivatives to necrotize cells of said diseased tissue.

Figure 2:
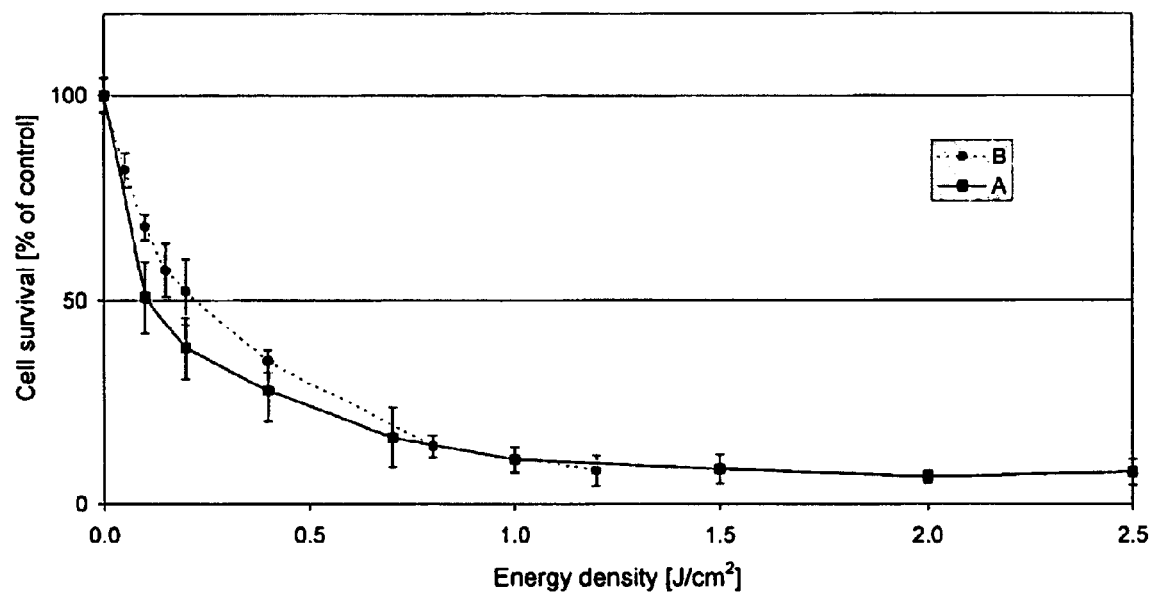
FIG. 2: Determination of phototoxicity (Example 15) of water-soluble salt of chlorin $e_6$ (7) with N-methyl-D-glucamine (10) being prepared (A) according to this invention (Example 9) and (B) according to Ponomarev (RU2144538); the test was performed in OV2774 cells under addition of different concentrations of the photosensitizer as indicated and irradiation at 670 nm.

Determination of dark toxicity (example 31, FIG. 1) and phototoxicity (example 32, FIG. 2) of one of the porphyrin derivatives of the present invention, namely the water-soluble salt of chlorin $e_6$ (7) with N-methyl-D-glucamine (10) prepared according to Example 9B, in cell culture experiments showed excellent properties of the compounds for use in PDT. The experiments were carried out to also demonstrate the inferior characteristics (higher dark toxicity and lower phototoxicity) of a same compound but being prepared according to the Ponomarev technology (RU2144538).

However, in special cases the administration of defined mixtures of hydrophilic amine salts of different porphyrin derivatives might be advantageous, if these mixtures display a higher phototoxicity towards the diseased tissue. This enhanced phototoxicity might be caused by the observed phenomenon of the enhancement of water solubility of the mixture of compounds (4), (7) and (8) as salts with hydrophilic amines in the presence of the same salts of chlorin $e_6$.

Other examples of good phototoxic properties of water-soluble forms of the present invention are provided in Tables 1 and 2 which summarize the results of dark and phototoxicity experiments in HeLa cells with water-soluble salts of acids (4), (7), (22), and (25) with N-methyl-D-glucamine (10).

It is another object of the present invention to use the disclosed water-soluble forms of chlorin and pheophorbide derivatives in anti-microbial photodynamic therapy. This is illustrated by the data presented in Table 3 which summarizes the results of photodynamic treatment of a number of micro organisms with water-soluble salts of acids (4), (7), (22), and (25) with N-methyl-D-glucamine (10).

EXAMPLES

The following examples are presented to provide those of ordinary skill in the art with a full and illustrative disclosure and description of how to make water-soluble porphyrin derivatives of the invention to be used in preparation of pharmaceutical compositions and are not intended to limit the scope of what the inventor regards as the invention. Efforts have been made to ensure accuracy with respect to numbers used (e.g. amounts, temperature etc.), but some experimental errors and deviations should be accounted for.

Examples 1

Obtaining Methyl Pheophorbide (5) from *Spirulina platensis*

(A) A mixture of 20 g of *Spirulina platensis*, 60 mL of methanol and 10 mL of concentrated sulfuric acid was stirred at room temperature for 3 hours, diluted with 30 mL of methanol and filtered through a pad of Celite. The content of the filtrating funnel was washed with methanol (70 mL). The above solution was extracted with hexane (2×30 mL), diluted with chloroform (100 mL) and poured into a saturated aqueous solution of potassium chloride (300 mL). The resulting mixture was filtered through a pad of Celite, aqueous phase was extracted with chloroform (2×50 mL). The combined extracts were washed with water, filtered through cotton and concentrated. The residue was dissolved in the mixture of chloroform-hexane (1:1, 30 mL) and filtrated through a pad of aluminum oxide to wash a first time with hexane (to remove non-polar non-chlorin components) and then with methylene chloride (to get methyl pheophorbide). Methylene chloride solution was concentrated and the residue was re-crystallized a first time from methylene chloride-methanol (3 mL+7 mL), re-crystallized a second time from methylene chloride-methanol (1 mL+10 mL), and finally washed with methanol (10 mL) to give 113 mg of pure methyl pheophorbide a (5). $^1$H—NMR spectrum: 9.41, 9.23, 8.56 (3H, all s, meso-H); 7.88 (1H, q, —CH═CH$_2$), 6.25–6.10 (2H, —CH═CH$_2$), 6.28 (1H, s, cyclopentanone-H), 4.50, 4.25 (2H, m, 7-H, 8-H); 3.55 (2H, q, 4-CH$_2$CH$_3$); 3.93, 3.70, 3.63, 3.39, 3.15 (15H, all s, 5 υ —CH$_3$); 2.75–2.20 (4H, m, —CH$_2$CH$_2$COOCH$_3$); 1.85 (3H, d, 8-CH$_3$); 1.71 (3H, m, 4-CH$_2$CH$_3$); 0.55 and –1.68 ppm (2H, 2 broad s, 2 υ —NH—). The product is identical to the same compound obtained from Porphyrin Products Inc., USA.

(B) A mixture of 10 g of Spirulinaplatensis, 30 mL of methanol, and 5 mL of conc. sulfuric acid was stirred at room temperature (r.t.) for 3 hours, diluted with cold water (70 mL), and filtered through a pad of Celite. The content of the filtrating funnel was washed with water up to pH 7, ethanol (50 mL), hexane (4×30 mL), and the required methyl pheophorbide was removed from the content of the filtrating funnel with acetone (120 mL). The above solution was concentrated, dissolved in chloroform, filtered through a pad of sodium sulfate (anhydrous), and concentrated. The residue was re-crystallized a first time from methylene chloride-methanol (1.5 mL+5 mL) and a second time from methylene chloride-methanol (1.5 mL+10 mL), and finally washed with methanol (15 mL) to give 60 mg of pure methyl pheophorbide a (5).

(C) $H_2SO_4$ (conc., 250 mL) was added at to a suspension of 500 g of Spirulina platensis in MeOH (1500 mL) at room temperature and under stirring. The mixture formed was kept at r.t. for 3 hours, then poured into water (6 L) and filtered through a pad of Celite (diam. 12 cm, height 2 cm; on filter Schott N3). The paste on the filter was washed with water (3×800 mL, until pH 6), then with ethanol (3×300 mL) and petroleum ether (40–60° C., 3×250 mL). Next, the target product was removed from the pad with acetone (in total 1.2 L), concentrated, dissolved in $CHCl_3$ (200 mL), filtered through cotton wool, then concentrated in vacuo and the residue was crystallized from a mixture of $CH_2Cl_2$ (40 mL) and MeOH (200 mL) to give 2.45 g of methyl pheophorbide a of ~90% purity (TLC in $CHCl_3$/acetone 95:5). The latter was dissolved in $CHCl_3$ (20 mL) and passed through a pad of $Al_2O_3$ (neutral, Grade II; d 8 cm, h 5 cm) by elution with $CHCl_3$; concentration and re-crystallization from a mixture of $CH_2Cl_2$ (50 mL) and MeOH (250 mL) gave 2.38 g of pure (TLC control) methyl pheophorbide a (5). Additional amounts of methyl pheophorbide a (~10–15%) can be obtained by a usual workup (chromatography and re-crystallization) of mother solutions from both crystallizations.

Example 2

Obtaining Ethyl Pheophorbide (6) from Spirulina platensis

Ethanolysis of 20 g of Spirulina platensis in 60 mL of 96% aqueous ethanol and 10 mL concentrated sulfuric acid and subsequent workup as described in the Example 1A for the preparation of methyl pheophorbide a (5) but with the use of ethanol instead of methanol in all steps, gave 110 mg of crystalline ethyl pheophorbide a (6). $^1$H—NMR spectrum: 9.57, 9.42, 8.61 (3H, all s, meso-H); 7.99 (1H, q, —CH═CH$_2$), 6.32, 6.26 (2H, dd, —CH═CH$_2$), 6.27 (1H, s, cyclopentanone-H), 4.51, 4.28 (2H, m, 7-H, 8-H); 4.07 (2H, q, —COOCH$_2$CH$_3$); 3.71 (2H, q, 4-CH$_2$CH$_3$); 3.89, 3.72, 3.41, 3.27 (12H, all s, 4 υ —CH$_3$); 2.69, 2.47, 2.37, 2.22 (4H, m, —CH$_2$CH$_2$COOCH$_2$CH$_3$); 1.83 (3H, d, 8-CH$_3$); 1.73 (3H, t, 4-CH$_2$CH$_3$); 1.12 (3H, t, —COOCH$_2$CH$_3$); 0.57, −1.46 ppm (2H, 2 broad s, 2 υ —NH—).

Example 3

Obtaining Methyl Pheophorbide a (5) from Spirulina maxima

A treatment of 10 g of Spirulina maxima with 30 mL of methanol and 5 mL of concentrated sulfuric acid and subsequent workups as described for preparation of methyl pheophorbide a (5) in Example 1B afforded to 64 mg of pure methyl pheophorbide a (5).

Example 4

Obtaining Methyl Pheophorbide a (5) and b (17) from Chlorella 10 g of dry biomass of Chlorella was subjected to methanolysis and subsequent workups as described in the Example 3 to produce a mixture (140 mg) of methyl pheophorbides a and b in the ratio 20:7 as determined by $^1$H NMR spectroscopy. Chromatography of the mixture obtained on the column with Silica gel 60 (Fluka, 70–230 mesh) with the elution chloroform-toluene-acetone 15:30:1.5 produced individual methyl pheophorbides a (5) and b (17). Methyl pheophorbides a (5) was identical to the products described above. $^1$H—NMR spectral data for methyl pheophorbide b (17): 11.0 (1H, s, CHO), 10.22, 9.50, 8.55 (3H, all s, meso-H); 7.98 (1H, q, —CH═CH$_2$), 6.40–6.15 (2H, —CH═CH$_2$), 6.25 (1H, s, cyclopentanone-H), 4.48, 4.20 (2H, m, 7-H, 8-H); 3.60 (2H, q, 4-CH$_2$CH$_3$); 3.93, 3.78, 3.75, 3.40 (12H, all s, 4 υ —CH$_3$); 2.75–2.20 (4H, m, —CH$_2$CH$_2$COOCH$_3$); 1.85 (3H, d, 8-CH$_3$); 1.71 (3H, m, 4-CH$_2$CH$_3$); 0.48 and −1.60 ppm (2H, 2 broad s, 2 υ —NH—).

Examples 5

Obtaining Methyl Pheophorbide a (5) and b (17) from Powdered Dry Nettle Leaves

Methanolysis of 500 g dried and powdered nettle leaves and subsequent workups as described in Example 1C produced a mixture (1.74 g) of methyl pheophorbides a (5) and b (17) in the ratio 6.5:1 as determined by $^1$H NMR spectroscopy.

Example 6

Obtaining Methyl Pheophorbide a (5) and b (17) from Frozen Spinach Leaves $H_2SO_4$ (conc., 5 mL) was added to a mixture of 100 g frozen spinach leaves and MeOH (100 mL) at r.t. and under stirring. The mixture formed was kept at r.t. for 16 hours, diluted with water (100 mL), and filtered through Celite. The residue was washed with acetone (3×50 mL), acetone extracts were diluted with $CH_2Cl_2$-water (1:1, 100 mL), the organic phase was separated and concentrated. The residue was subjected to methanolysis in 100 mL of 5% conc. $H_2SO_4$ in MeOH, and subsequent workups as described in Example 1C gave 40 mg of the mixture of methyl pheophorbides a (5) and b (17) in the ratio 2:1 as determined by $^1$H NMR spectroscopy.

Example 7

Preparation of methyl 2-devinyl-2-(1-ethoxyethyl)-pheophorbide a (18)

Methyl pheophorbide a (5) 3.5 g (5.8 mmol) was dissolved in a mixture of hydrogen bromide and acetic acid (d 1.44, 50 mL) and left for 18 hours. The mixture was then evaporated to dryness at 50° C. in vacuo, and absolute ethanol (100 mL) was added under stirring. After 18 hours, the reaction mixture was poured onto crushed ice under stirring and extracted with $CH_2Cl_2$ (3×40 mL). The combined extract was washed with water (4×70 mL) and evaporated to dryness in vacuo. The residue was subjected to column chromatography on silicagel (40–63 μm, Merck) with eluting by $CH_2Cl_2$ to give 2.95 g of product (18), yield 77%. $^1$H—NMR spectrum: 9.82, 9.58, 8.55 (3H, all s, meso-H); 6.31 (1H, s, 10-H), 5.96 (1H, q, 2-CHCH$_3$); 4.53, 4.25 (2H, m, 7-H, 8-H); 3.71 (4H, dq, 4-CH$_2$CH$_3$, —OCH$_2$CH$_3$); 3.93, 3.87, 3.63, 3.41, 3.28 (15H, all s, 5 υ —CH$_3$); 2.67, 2.51, 2.37, 2.23 (4H, m, —CH$_2$CH$_2$COOCH$_3$); 2.11 (3H, d, 2-CHCH$_3$); 1.80 (3H, d, 8-CH$_3$); 1.75 (3H, t, 4-CH$_2$CH$_3$); 1.36 (3H, t, —OCH$_2$CH$_3$); 0.55, −1.41 (2H, 2 broad s, 2 υ —NH).

Example 8

Preparation of Chlorin $e_6$ (7)

An aqueous solution of KOH (degassed, 10%-soln, 10 mL) was added to a stirred solution of 140 mg (231 µmoles) methyl pheophorbide a (35) in degassed (with helium) acetone (12 mL) under argon. The mixture was stirred for 40 min under 40° C., heated up to 65° C., and then a 3% aqueous solution of KOH (prepared from 5 mL of degassed 10% aq. KOH and 11 mL of degassed water) was added. The resulting mixture was stirred for 2.5 hours under argon and heated at 65° C., then cooled to r.t., diluted with 100 mL of water, and acidified with 2 N HCl (12 mL). The precipitate was then separated by centrifugation (3 min at 5000 rpm), washed with water (3×30 mL) with re-centrifugation, re-suspended in 10 mL of water and freeze dried to give crude chlorin e6 (120 mg, 87%, ~90% purity, controlled with TLC) as free acid. TLC: RP-18 TLC plates (Merck), MeOH—$CH_2Cl_2$ (3:1), Rf 0.6; contaminants: more polar impurities with Rf <0.3. Final purification: 20 mg of crude chlorin e6 was dissolved in MeOH—$CH_2Cl_2$-water (3:1:1, 4 mL) and subjected to MPLC on RP-8 column (Merck, #11447, 240×10, 40–63 Пm) with elution by MeOH—$CH_2Cl_2$-water (4:3:1, 2 mL/min) to give pure chlorin e6 (7) (15 mg, 75%). A contaminant impurity was eluted with MeOH—$CH_2Cl_2$ (3:1). $^1$H—NMR spectrum (DMSO-$d_6$): 9.88, 9.78, 9.18 (3H, all s, meso-H); 8.33 (1H, dd, —CH═$CH_2$); 6.47 (1H, d, cis —CH═$CH_2$); 6.22 (1H, d, trans —CH═$CH_2$); 5.38 (2H, m, —$CH_2$COOH); 4.62 (1H, m, —$CHCH_3$); 4.48 (1H, m, —$CHCH_2$); 3.83 (2H, m, —$CH_2CH_3$); 3.59, 3.53, 3.33 (9H, all s, —$CH_3$); 2.62, 2.27, 2.14, (4H, m, —$CH_2CH_2$COOH); 1.70, 1.66 (6H, m, —$CHCH_3$+—$CH_2CH_3$); 1.64, -1.90 (2H, 2 broad s with different intensity, 2 υ —NH—). $^{13}$C—NMR spectrum (DMSO-$d_6$) characteristic signals only: 174.15, 173.46, 172.34 (COOH); 129.21 (—CH═$CH_2$); 122.25 (—CH═$CH_2$); 103.74 (Θ); 101.12 (E); 98.09 (Δ); 94.67 (Γ); 52.66 ($CHCH_2$); 48.19 ($CHCH_3$); 37.80 (—$CH_2$COOH); 30.82, 29.50 (—$CHCH_2CH_2$COOH); 22.92 ($CHCH_3$); 18.91 ($CH_2CH_3$); 17.58 ($CH_2CH_3$); 11.00, 10.98 (ArMe).

Example 9

Preparation of Water-soluble Salt of Chlorin $e_6$ (7) with N-methyl-D-glucamine (10)

(A) A solution of N-methyl-D-glucamine (10) (4 mg, 21 lmol) in water (4 mL) was added to a solution of 5 mg (8.4 µmol) chlorin $e_6$ (7) in MeOH—$CH_2Cl_2$ (3:1, 20 mL) (or in acetone), and organic solvents were evaporated off in vacuo. The resulting aqueous solution was filtered through a membrane (20 µm) and freeze dried to yield the water-soluble salt (9 mg, includes the excess of N-methyl-D-glucamine) quantitatively.

(B) A 10% aqueous degassed solution of potassium hydroxide (10 mL) was added to a solution of 50 mg of methyl pheophorbide a (5) in degassed acetone (12 mL). The mixture was stirred at 40° C. for 30 minutes under inert atmosphere (argon) followed by the addition of 15 mL of 3% aqueous degassed solution of potassium hydroxide. The resulting mixture was stirred at 65° C. for 2 hours under inert atmosphere (argon) then diluted with water (100 mL), and chlorine $e_6$ (7) was precipitated by the addition of 2N aqueous solution of HCl (up to pH 6). The precipitate was separated by centrifugation (3000 rpm for 5 minutes), washed with water (3×10 mL) resulting in a wet paste of chlorin $e_6$ that was used in the next step directly, without additional purification. The whole sample of the obtained chlorin $e_6$ (7) was mixed under argon with N-methyl-D-glucamine (10) (30 mg., 2 eq.) and water (10 mL) to get about 5% solution of the water-soluble salt. The resulting mixture was stirred until it completely dissolved, evaporated to dryness and subjected to further HPLC on the column with RP C-8 in water-methanol gradient (from 40% to 80%). Samples of the mixture containing the target product were collected and lyophilized to give water-soluble bis-salt in about 75–80% yield. Its structure was confirmed by $^1$H NMR spectroscopy. Particularly, a 1:2 ratio of chlorin e6 (7) to N-methyl-D-glucamine (10) moieties was confirmed by integration of the signals of the N-Me group in glucamine component (at 2.70 ppm) and 8-Me group of chlorin unit (at 1.75 ppm).

(C) The mixture of 50 mg (84 µmol) of powdered chlorin $e_6$ (7), 40 mg (0.21 mmol), N-methyl-D-glucamine (10) and water (50 mL, preliminary degassed with inert gas) was stirred under argon and in darkness until completely dissolved. The resulting solution was filtered through a membrane (20 µm) and freeze dried to give the water-soluble salt (90 mg, includes the excess of N-methyl-D-glucamine) quantitatively.

Example 10

Preparation of 2-devinyl-2-(1-ethoxyethyl)-chlorin $e_6$ (19)

Methyl 2-devinyl-2-(1-ethoxyethyl)-pheophorbide a (18) (2.8 g, 4.1 mmol) was subjected to saponification as described for the preparation of chlorin $e_6$ (Example 8) to yield, after column chromatography, 2.1 g of product (19), yield 79%. $^1$H—NMR spectrum (DMSO-$d_6$): 9.88, 9.78, 9.18 (3H, all s, meso-H); 6.47 (1H, d, cis —CH═$CH_2$); 6.22 (1H, d, trans —CH═$CH_2$); 5.5.1 (2H, m, —$OCH_2CH_3$); 5.38 (2H, m, —$CH_2$COOH); 4.62 (1H, m, —$CHCH_3$); 4.48 (1H, m, —$CHCH_2$); 4.29 (1H, q, —$CHCH_3$); 3.83 (2H, m, —$CH_2CH_3$); 3.59, 3.53, 3.33 (9H, all s, —$CH_3$); 2.62, 2.27, 2.14, (4H, m, —$CH_2CH_2$COOH); 1.83 (1H, d, —CH(O—)$CH_3$); 1.70, 1.66 (6H, m, —$CHCH_3$+—$CH_2CH_3$); 1.54 (3H, t, —$OCH_2CH_3$); -1.90 (2H, 2 broad s with different intensity, 2 υ —NH—). $^{13}$C—NMR spectrum (DMSO-$d_6$) characteristic signals only: 174.15, 173.46, 172.34 (COOH); 129.21 (—CH═$CH_2$); 103.74 (Θ); 101.12 (E); 98.09 (Δ); 94.67 (Γ); 67.97 (—CH(O—)$CH_3$); 63.49 (—$OCH_2CH_3$); 52.66 ($CHCH_2$); 48.19 ($CHCH_3$); 37.80 (—$CH_2$COOH); 30.82, 29.50 (—$CHCH_2CH_2$COOH); 22.92 ($CHCH_3$); 20.20 (—CH(O—)$CH_3$); 18.91 ($CH_2CH_3$); 17.58, 15.23 ($CH_2CH_3$+—$OCH_2CH_3$); 11.00, 10.98 (ArMe).

Example 11

Preparation of the Water-soluble Salt of Chlorin $e_6$ Derivative (19) with N-methyl-D-glucamine (10)

Reaction of 30 mg of 2-devinyl-2-(1-etoxyethyl)-chlorin $e_6$ (19) with 20 mg of N-methyl-D-glucamin (10) as described in Example 9C gave 50 mg of freeze dried water-soluble salt quantitatively.

Example 12

Preparation of bis[2-(E-maltosyloxy)ethyl]amine (11)

A solution of per-O-acetyl-maltosylbromide (500 mg, 0.7 mmol), N-benzyloxycarbonyl-N,N-bis(2-hydroxyethyl)

amine (56 mg, 0.233 mmol) and 2,4,6-trimethylpyridine (80 Π, 0.605 mmol) was added drop wise to a stirred mixture of silver trifluoromethanesulfonate (208 mg, 0.805 mmol) and 1.5 mL of absolute $CH_2Cl_2$ at −20° C. The mixture was left to warm to r.t., then was treated with 0.5 mL of triethylamine, diluted with 200 mL of dichloromethane, washed with saturated aqueous solution of $Na_2S_2O_3$ (50 mL) and water (50 mL), concentrated and subjected to flash chromatography in ethyl acetate-petroleum ether (1:1) to give crude N-benzyloxycarbonyl-N,N-bis[2-(hepta-O-acetyl-E-maltosyloxy)ethyl]amine (57 mg). Selected structure specific $^{13}C$ NMR data (500 MHz, $CDCl_3$): 20.41 ($CH_3CO$); 46.92, 47.24, 48.00 and 48.02 ($OCH_2CH_2N$ and $OCH_2CH_2N$); 61.30, 61.50, 61.98, and 62.52 (C-6 of glucose moieties); 67.18 ($NCOOCH_2C_6H_5$); 67,81, 68,33, 69.14, 69.84, 72.02, 72.55, 75.10 (C-2-C-5 of glucose moieties); 95.38 (C-1 of Δ-glucose moieties); 100.18 and 101.10 (C-1 of E-glucose moieties); 127.73, 128.01 and 128.40 ($OCH_2C_6H_5$); 164.00 (NCOO); 169,24,169.42, 169.76, 169.98, 170.35 ($CH_3CO$). $[\Delta]_D$ 38.9°(c 1, ethyl acetate). The product obtained was dissolved in 0.1 M sodium methylate in absolute methanol and kept for 2 hours, then was neutralized with ion-exchange resin KU-2($H^+$) and filtered. The filtrate was subjected to hydrogenolysis under Pd/C overnight, filtered, and freeze dried to yield 23 mg of compound (11), $[\Delta]_D$ 710 (c 1, water). Selected structure specific $^{13}C$ NMR data (500 MHz, $D_2O$): 48.74 ($OCH_2CH_2N$), 50.85 ($OCH_2CH_2N$); 61.72 (C-6 of Δ-glucose moieties), 61.92 (C-6 of E-glucose moieties), 77.28 (C-4 of E-glucose moieties); 100.83 (C-1 of Δ-glucose moieties); 103.40 (C-1 of E-glucose moieties).

Example 13

Preparation of Water-soluble Salt of Chlorin $e_6$ (7) with bis[2-(E-maltosyloxy)ethyl]amine (11)

Reaction of 5 mg of chlorin $e_6$ (7) with 18.6 mg of amine (11) as described in Example 9C gave 23 mg of freeze dried water-soluble salt almost quantitatively.

Example 14

Obtaining Methyl mesopheophorbide-a (37)

Methyl pheophorbide-a (5) (130 mg, 0.2 mmol) was dissolved in 5 mL of tetrahydrofuran and hydrogenated at ~1 atm of $H_2$ over 30 mg of 10% $Pd(OH)_2$ on carbon for 1 hour at room temperature. Catalyst was filtered and the solution was concentrated to give pure methyl mesopyropheophorbide-a (37) (125 mg, quantitative).

Example 15

Obtaining mesochlorin-$e_6$ (20)

Alkaline hydrolysis of methyl mesopheophorbide-a (37) (20 mg, 0.033 mmol) as described in Example 9B produced mesochlorin-$e_6$ (17 mg, 86%). MS(−)(electrospray): 597.3 (M−H).

Example 16

Preparation of Water-soluble Salt of Mesochlorin $e_6$ (20) with N-methyl-D-glucamine (10)

Reaction of 15 mg of mesochlorin $e_6$ (20) with 12 mg of N-methyl-D-glucamine (10) as described in Example 9C produced 27 mg of freeze dried water-soluble salt quantitatively.

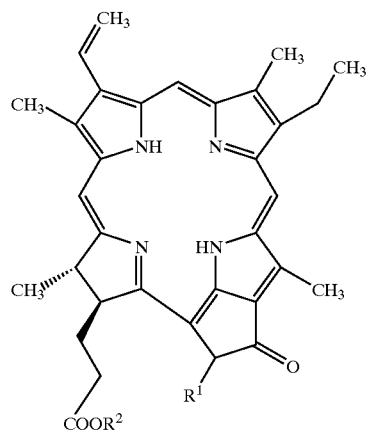

(37) $R^1$ = COOMe, $R^2$ = Me
(40) $R^1$ = H, $R^2$ = Me
(41) $R^1$ = H, $R^2$ = $C_6F_5$

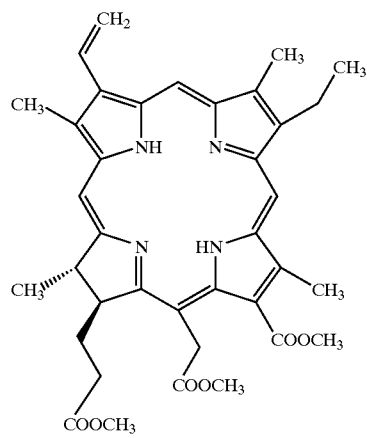

(38)

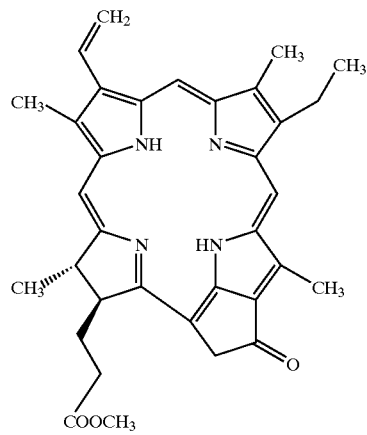

(39)

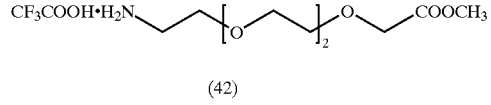

(42)

-continued

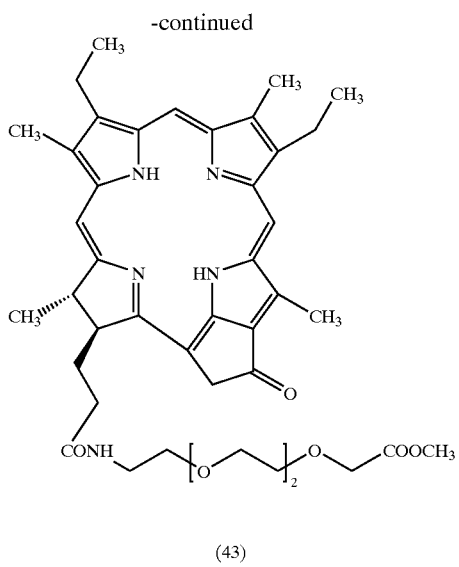

(43)

Example 17

Preparation of Water-soluble Salt of Pheophorbide a (4) with N-methyl-D-glucamine (10)

Methyl pheophorbide a (5) (30 mg, 0.049 mmol) was dissolved in 2 mL of 50% sulfuric acid and the mixture was stirred at room temperature for 2 hours, diluted with ice-cold water, and extracted with chloroform. The extracts were washed with water, dried over anhydrous $Na_2SO_4$, and concentrated to give crude pheophorbide-a (4). The latter was then dissolved in a 3 mL N-methyl-D-glucamine (10) (11.6 mg, 1.2 eq.) aqueous solution. The resulting solution was filtered through a 45 IIm filter and freeze dried to give 29 mg of freeze dried water-soluble salt. MS(−) (electrospray) (acid 4 component): 591.2 (M−H).

Example 18

Preparation of Water-soluble Salt of Dimethyl Chlorin $e_6$ Dimethyl Ester (21) with N-methyl-D-glucamine (10)

Acidic hydrolysis of trimethyl ester of chlorin-$e_6$ trimethyl ester (38) [prepared according to Lötjönen S., Hynninen P. H., *Synthesis*, 1980, 541–543] (25 mg, 0.039 mmol) with 50% sulfuric acid, and reaction with 9 mg of N-methyl-D-glucamine (10) as described in Example 17 resulted in 32 mg of freeze dried water-soluble salt. MS(−)(electrospray) (acid 21 component): 623.5 (M−H).

Example 19

Preparation of Water-soluble Salt of Mesopyropheophorbide a Derivative (25) with N-methyl-D-glucamine (10)

Methyl pheophorbide-a (5) (1.3 g, 2.09 mmol) was dissolved in 100 mL of pyridine and stirred at reflux for 8 hours under nitrogen in the dark. Pyridine was removed by evaporation and the residue was recrystallized from dichloromethane/methanol to give 1.08 g (92%) of methyl pyropheophorbide-a (39). UV/vis $O_{max}$ (H)($CH_2Cl_2$): 410 (112500), 509 (11400), 537 (9800), 611 (8500), 669 (47000) nm.

Methyl pyropheophorbide a (39) (1.0 g, 1.78 mmol) was dissolved in 100 mL of acetone and hydrogenated at ~8–10 atm of $H_2$ over 300 mg of 10% Pd on carbon for 2 hours at room temperature. The catalyst was filtered out and the solution was concentrated to give pure methyl mesopyropheophorbide a (40) (1.0 g, quant.). UV/vis $O_{max}$ (H) ($CH_2Cl_2$): 408 (136000), 501 (12400), 534 (11800), 603 (10500), 656 (54600) nm; $^1$H—NMR (200 MHz, $CDCl_3$): 9.40 (s, 1 H, E-meso H), 9.16 (s, 1 H, Δ-meso H), 8.46 (s, 1 H, Γ-meso H), 5.26 and 5.08 (AB, J=19.7 Hz, 10-$CH_2$), 4.46 (dq, 1 H, $J_{7,8}$=2.0 Hz, 8-H), 4.27 (dt, 1 H, 7-H), 3.80 and 3.63 (each q, 4 H, J=7.5 Hz, 2a- and 4a-$CH_2$), 3.63, 3.52, 3.28 and 3.21 (each s, 12 H, 1-, 3-, 5-Me and COOMe), 2.80-2.20 (m, 4 H, 7a,b-$CH_2CH_2$), 1.80 (d, 3 H, J=7.3 Hz, 8-Me), 1.71 and 1.63 (each t, 6 H, J=7.5 Hz, 2b- and 4b-Me), 0.60 and −1.60 (each br s, 2 H, NH).

Methyl mesopyropheophorbide a (40) (250 mg, 0.443 mmol) was dissolved in 5 mL of 50% sulfuric acid and the mixture was stirred at room temperature for 2 hours, diluted with ice-cold water, and extracted with chloroform. These extracts were washed with water, dried over anhydrous $Na_2SO_4$, and concentrated to give crude mesopyropheophorbide a (36). The latter was dissolved in 20 mL of dichloromethane, then 0.3 mL (2.22 mmol, ~5 eq.) of triethylamine was added followed by addition of 0.1 mL (0.576 mmol, 1.3 eq.) of pentafluorophenyl trifluoroacetate. The mixture was stirred at room temperature for 20 min (to produce compound 41), 0.5 mL of water was added followed by addition of a solution of compound 42 (200 mg, product of GlycoSense AG, Jena, Germany) in 5 mL of dichloromethane. The mixture was stirred at room temperature for 30 min, diluted with dichloromethane, then washed with water and 5% sulfuric acid, dried, and concentrated. The residue was purified by flash chromatography on Silica gel. Elution with acetone-dicloromethane (20:80) gave 290 mg (88%) of amide 43. UV/vis $O_{max}$ (H) ($CH_2Cl_2$): 408 (136500), 501 (12300), 534 (11800), 603 (10000), 656 (54500) nm; $^1$H—NMR (300 MHz, $CDCl_3$): 9.41 (s, 1 H, E-meso H), 9.20 (s, 1 H, Δ-meso H), 8.47 (s, 1 H, Γ-meso H), 6.08 (br s, 1 H, CONH), 5.26 and 5.08 (AB, J=19.7 Hz, 10-$CH_2$), 4.51 (br q, 1 H, 8-H), 4.32 (br d, 1 H, 7-H), 3.82 and 3.66 (each q, 4 H, J=7.5 Hz, 2a- and 4a-$CH_2$), 3.78 (s, 2 H, OC$H_2$COOMe), 3.63, 3.32 and 3.21 (each s, 9 H, 1-, 3- and 5-Me), 3.52 (s, 3 H, COOMe), 3.28 (br s, 12 H, NHC$H_2$C$H_2$OC$H_2$C$H_2$OC$H_2$C$H_2$O), 2.80–1.90 (m, 4 H, 7a,b-$CH_2CH_2$), 1.80 (d, 3 H, J=7.3 Hz, 8-Me), 1.72 and 1.68 (each t, 6 H, J=7.5 Hz, 2b- and 4b-Me), 0.70 and −1.60 (each br s, 2 H, NH). $^{13}$C—NMR (75 MHz, $CDCl_3$): 196.3, 172.4, 172.3, 160.2, 155.2, 150.3, 149.0, 145.0, 142.3, 141.6, 137.3, 136.9, 135.6, 131.3, 130.1, 127.8, 105.9, 104.1, 95.8, 92.5, 70.5, 70.2, 69.9, 69.6, 68.2, 51.6, 50.1, 48.0, 39.1, 39.0, 32.6, 30.2, 23.1, 19.5, 19.4, 17.5, 17.0, 12.0, 11.3, 11.0.

Amide 43 (195 mg, 0.263 mmol) was dissolved in 4 mL of 50% sulfuric acid and the mixture was stirred at room temperature for 2 hours, diluted with ice-cold water, The resulting precipitate was separated by centrifugation (5000 rpm for 3 min), washed with water (2×50 mL) up to pH 7 (25 formation), and dissolved in a mixture of acetone (50 mL), methanol (15 mL) and water (6 mL). N-methyl-D-glucamine (10) (56 mg, 0.29 mmol, 1.1 eq.) was then added to the above solution. The resulting solution was concen trated at 40° C. in vacuum (~20 mmHg) to remove organic solvents. The residue of the concentration process was dissolved in 40 mL of water, filtered through 45 Πm filter, and freeze dried to yield 239 mg of water-soluble salt. UV/vis O$_{max}$ (H)(H$_2$O): 375 (46550), 514 (5750), 548 (5750), 608 (6320), 660 (21260).MS(−)(electrospray) (acid 25 component): 724.7 (M−H)

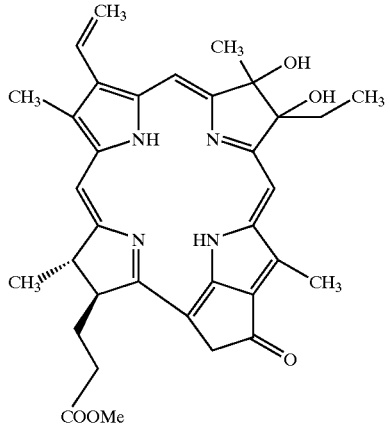

(44)

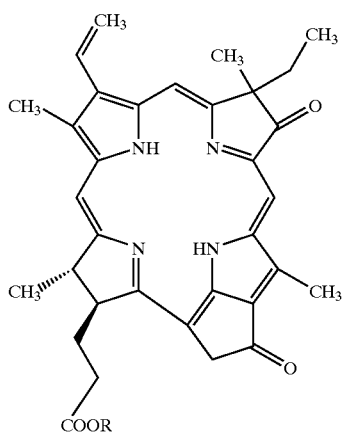

(45) R = Me
(46) R = H
(47) R = C$_6$F$_5$

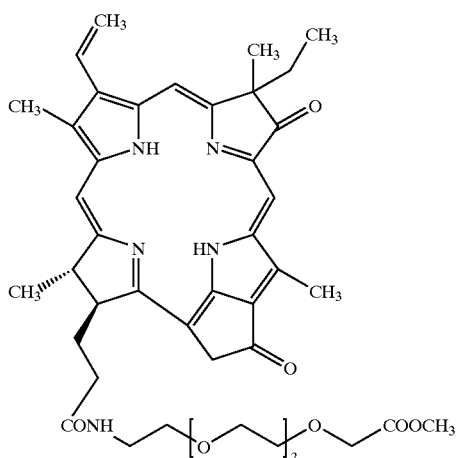

(48)

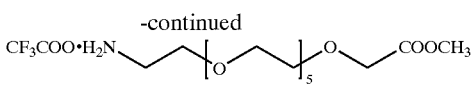

(49)

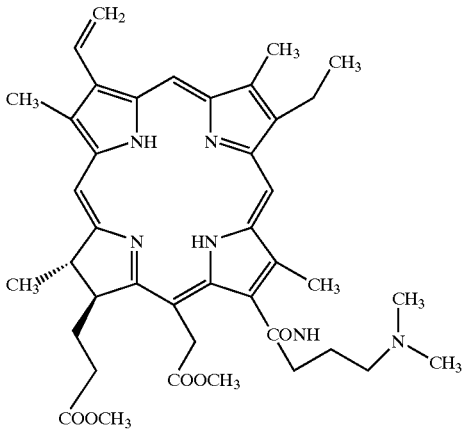

(50)

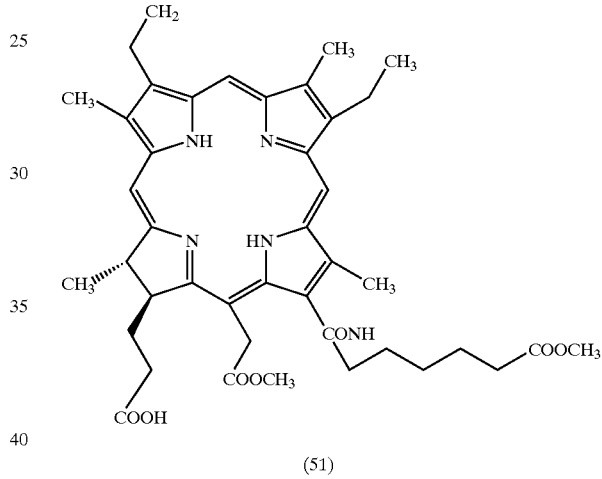

(51)

Example 20

Preparation of Water-soluble Salt of Bacteriopheophorbide Derivative (29) with N-methyl-D-glucamine (10)

0.5 mL of pyridine was added to a stirred solution of methyl mesopyropheophorbide-a (40) (650 mg, 1.152 mmol) in 130 mL of dichlorometane, followed by addition of 600 mg (2.361 mmol, 2.05 eq.) of osmium tetroxide. The reaction mixture was stirred at room temperature for 48 hours, H$_2$S was then bubbled through the solution for 5 min to transform osmate into free diol (44), and the mixture was separated on Silica gel. Elution with acetone-chloroform (5:95) gave starting compound 40 (190 mg, 29%). Elution with acetone-chloroform (15:85) gave diol (44) (350 mg, 51%). The latter was treated with 20 mL of conc. H$_2$SO$_4$ for 30 min at room temperature. The reaction mixture was diluted with ice-cold water, and extracted with chloroform. The extracts were washed with aqueous sodium bicarbonate and water, dried over anhydrous Na$_2$SO$_4$, and concentrated. The residue was purified by column chromatography on Silica gel. Elution with acetone-chloroform (1:99) produced ketone (45) (180 mg, 27% starting from (40)) [cf. R. K. Pandey et al., *J. Org. Chem.*, 1997, 62, 1463–1472]. The latter was dissolved in 5 mL of 50% sulfuric acid and that mixture was stirred at room temperature for 2 hours, diluted with ice-cold water, and extracted with chloroform. The extracts were washed with water, dried over anhydrous $Na_2SO_4$, and concentrated to give crude compound 46. The latter was dissolved in 20 mL of dichloromethane, 0.2 mL (1.58 mmol, ~5 eq.) of triethylamine was added followed by addition of 70 Π (0.411 mmol, 1.3 eq.) of pentafluorophenyl trifluoroacetate. The mixture was stirred at room temperature for 20 min (to give 47), and 0.5 mL of water was then added followed by addition of a solution of compound 42 (150 mg, product of GlycoSense AG, Jena, Germany) in 5 mL of dichloromethane. The mixture was stirred at room temperature for 30 min, diluted with dichloromethane, washed with water and 5% sulfuric acid, dried, and concentrated. The residue was purified by flash chromatography on Silica gel. Elution with acetone-dicloromethane (20:80) gave 205 mg (85%) of amide (48). UV/vis $O_{max}$ (H) ($CH_2Cl_2$): 394 (42300), 412 (44100), 506 (7650), 539 (9100), 597 (4500), 652 (15750), 712 (30600) nm; $^1$H—NMR (250 MHz, $CDCl_3$); 9.18, 8.72, 8.50 (each s, 3 H, meso H), 6.10 (br s, 1 H, CONH), 5.20 (m, 2 H, 10-$CH_2$), 4.50 and 4.30 (both m, 2 H, 8-H and 7-H), 3.88 (s, 2 H, $OCH_2COOMe$), 3.58, 3.41 and 3.21 (each s, 9 H, 1-, 3-and 5-Me), 3.51 (s, 3 H, COOMe), 3.30 (br s, 12 H, $NHCH_2CH_2OCH_2CH_2OCH_2CH_2O$), 2.80–1.90 (m, 4 H, 7a,b-$CH_2CH_2$), 1.90–1.65 (m, 6 H, 2×$CH_2CH_3$), 0.5 (m, 3 H, $CH_2CH_3$), −0.10 and −1.70 (each br s, 2 H, NH). $^{13}$C—NMR (75 MHz, $CDCl_3$): 201.4, 199.2, 172.3, 171.7, 153.3, 141.0, 137/2, 98.2, 95.0, 91.3, 89.7, 87.1, 79.4, 70.7, 70.4, 70.1, 69.8, 68.4, 53.4, 51.8, 49.9, 48.0, 39.3, 36.2, 32.9, 32.1, 30.5, 28.5, 25.9, 23.2, 19.3, 16.9, 11.9, 11.0, 9.0, 8.1.

Amide derivative (48) (205 mg, 0.270 mmol) was dissolved in 4 mL of 50% sulfuric acid and the mixture was stirred at room temperature for 2 hours, diluted with ice-cold water. The resulting precipitate was separated by centrifugation (5000 rpm for 3 min), washed with water (2×50 mL) up to pH 7 (to give 29), and dissolved in a mixture of acetone (50 mL), methanol (15 mL) and water (6 mL). N-Methyl-D-glucamine (10) (56 mg, 0.29 mmol, 1.1 eq.) was added to this solution. The resulting solution was concentrated at 40° C. in vacuum (~20 mmHg) to remove organic solvents. The residue was dissolved in 40 mL of water, filtered through a 45 Πm filter, and the solution was concentrated at 40° C. in vacuum (~20 mmHg) and dried at 40° C. in vacuum (~1 mmHg) to yield 240 mg of water-soluble salt. UV/vis $O_{max}$ (H)($H_2O$): 420 (40400), 515 (5380), 561 (6150), 668 (9610), 776 (51200). MS(−)(electrospray) (acid 29 component): 740.7 (M–H).

Example 21

Preparation of Water-soluble Salt of Pheophorbide a Ferivative (22) with N-methyl-D-glucamine (10)

Activation of pheophorbide a (4) (17 mg, 0.028 mmol) with pentafluorophenyl trifluoroacetate (15 Π) followed by reaction with compound 42 (25 mg, product of GlycoSense AG, Jena, Germany) in the presence of an excess of triethylamine, followed by acidic hydrolysis with 50% sulfuric acid and reaction with 6.5 mg of N-methyl-D-glucamine (10) as described in Example 19 gave 23 mg of freeze dried water-soluble salt. MS(−)(electrospray) (acid 22 component): 780.1 (M–H).

Example 22

Preparation of Water-soluble Salt of Pyropheophorbide a Derivative (23) with N-methyl-D-glucamine (10)

Acidic hydrolysis of methyl pyropheophorbide a (39) (15 mg) with 50% sulfuric acid, followed by activation with pentafluorophenyl trifluoroacetate (15 Π) and reaction with compound 42 (25 mg, product of GlycoSense AG, Jena, Germany) in the presence of an excess of triethylamine, and then followed by acidic hydrolysis with 50% sulfuric acid and reaction with 6 mg of N-methyl-D-glucamine (10) as described in Example 19 yielded 19 mg of freeze dried water-soluble salt. MS(−)(electrospray) (acid 23 component): 722.1 (M–H).

Example 23

Preparation of Water-soluble Salt of Mesopheophorbide a Derivative (24) with N-methyl-D-glucamine (10)

Acidic hydrolysis of methyl mesopheophorbide-a (37) (16 mg) with 50% sulfuric acid, followed by activation with pentafluorophenyl trifluoroacetate (15 Π) and reaction with compound 42 (25 mg, product of GlycoSense AG, Jena, Germany) in the presence of an excess of triethylamine, and then followed by acidic hydrolysis with 50% sulfuric acid and reaction with 6 mg of N-methyl-D-glucamine (10) as described in Example 19 yielded 18 mg of freeze dried water-soluble salt. MS(−)(electrospray) (acid 24 component): 782.2 (M–H).

Example 24

Preparation of Water-soluble Salt of Mesopyropheophorbide a Derivative (26) with N-methyl-D-glucamine (10)

Activation of mesopyropheophorbide a (36) (20 mg, 0.034 mmol) with pentafluorophenyl trifluoroacetate (20 Π) followed by reaction with compound 49 (40 mg, product of GlycoSense AG, Jena, Germany) in the presence of an excess of triethylamine, and reaction with 7 mg of N-methyl-D-glucamine (10) as described in Example 19 yielded 32 mg of freeze dried water-soluble salt. MS(−) (electrospray) (acid 26 component): 856.7 (M–H).

Example 25

Preparation of Water-soluble Salt of Mesopyropheophorbide a Derivative (27) with N-methyl-D-glucamine (10)

Activation of mesopyropheophorbide a (36) (15 mg, 0.026 mmol) with pentafluorophenyl trifluoroacetate (15 Π) followed by reaction with 20 mg of glycine methyl ester in the presence of an excess of triethylamine, then followed by acidic hydrolysis with 50% sulfuric acid and reaction with 5 mg of N-methyl-D-glucamine (10) as described in Example 19 yielded 19 mg of freeze dried water-soluble salt. MS(−) (electrospray) (acid 27 component): 592.6 (M–H).

Example 26

Preparation of Water-soluble Salt of Mesopyropheophorbide a Derivative (28) with N-methyl-D-glucamine (10)

Activation of mesopyropheophorbide-a (36) (14 mg, 0.024 mmol) with pentafluorophenyl trifluoroacetate (15 Π) followed by reaction with 25 mg of liaminocaproic acid methyl ester in the presence of an excess of triethylamine, then followed by acidic hydrolysis with 50% sulfuric acid and reaction with 5 mg of N-methyl-D-glucamine (10) as described in Example 19 yielded 20 mg of freeze dried water-soluble salt. MS(−)(electrospray) (acid 28 component): 648.5 (M–H).

Example 27

Preparation of Water-soluble Salt of Chlorin-e$_6$ Derivative (30) with N-methyl-D-glucamine (10)

A mixture of methyl pheophorbide a (5) (38 mg, 0.063 mmol) and N,N-dimethyl-1,3-diaminopropane (100 Π) in 1,4-dioxane (3 mL) was kept at room temperature for 10 hours (to produce compound 50). To this solution 6M NaOH aqueous solution (0.1 mL) was added and the resulting mixture was refluxed for 10 min. 5 mL of water was then added and refluxing was continued for additional 10 min. The mixture was cooled, diluted with 30 mL of water, and acidified with acetic acid up to pH 4.5. The precipitate formed was separated by centrifugation (5000 rpm for 3 min) then washed with water to yield diacid derivative (30). The/latter was dissolved in a 7 mL N-methyl-D-glucamine (10) (30 mg, 1.2 eq.) aqueous solution. The resulting solution was filtered through a 45 Πm filter and freeze dried to give 62 mg of water-soluble salt. MS(+)(electrospray) (acid 30 component): 681.3 (M+H).

Example 28

Preparation of Water-soluble Salt of Chlorin e$_6$ Derivative (31) with N-methyl-D-glucamine (10)

Reaction of methyl pheophorbide a (5) (22 mg, 0.036 mmol) with 1,7-diaminoheptane (100 Π), followed by alkaline hydrolysis with NaOH aqueous solution and reaction with 18 mg of N-methyl-D-glucamine (10) as described in Example 27 yielded 41 mg of freeze dried water-soluble salt. MS(-)(electrospray) (acid 31 component): 709.4 (M+H).

Example 29

Preparation of Water-soluble Salt of Chlorin e$_6$ Derivative (32) with N-methyl-D-glucamine (10)

A solution of pheophorbide a (4) (20 mg, 0.033 mmol) and Haminocaproic acid methyl ester (50 mg, ~10 eq.) in 1.4-dioxane (3 mL) was kept at room temperature for 120 hours. The mixture was diluted with dichloromethane, washed with 0.5N HCl aqueous solution and water, dried, concentrated, and purified by flash chromatography on Silica gel. Elution with 3% MeOH-dicloromethane produced 22 mg (88%) of amide derivative (51). Acidic hydrolysis of the latter with 50% sulfuric acid, and reaction with 13.5 mg of N-methyl-D-glucamine (10) as described in Example 17 yielded 33 mg of freeze dried water-soluble salt. MS(-)(electrospray) (acid 32 component): 722.3 (M–H).

Example 30

Preparation of Water-soluble Salt of Chlorin e$_6$ Derivative (33) with N-methyl-D-glucamine (10)

A solution of pheophorbide a (4) (20 mg, 0.034 mmol) and 2-aminoethanol (50 rL) in 1,4-dioxane (3 mL) was kept at room temperature for 1 hour. The mixture was diluted with dichloromethane, washed with 0.5N HCl aqueous solution and water, dried, concentrated, and purified by flash chromatography on Silica gel. Elution with 3% MeOH-dicloromethane produced 20 mg (91%) of amide derivative 33. Reaction with 8 mg of N-methyl-D-glucamine (10) as described in Example 17 yielded 28 mg of freeze dried water-soluble salt. MS(-)(electrospray) (acid 33 component): 652.2 (M–H).

Example 31

Determination of Dark Toxicity (Cytotoxicity) in OV2774 Cells of Water-soluble Salt of Chlorin e$_6$ (7) with N-methyl-D-glucamine (10) Prepared According to the Present Invention Versus that Produced According to Ponomarev et al (RU2144538)

To determine cytotoxicity (dark toxicity) of the water-soluble salt of chlorin e$_6$ (7) with N-methyl-D-glucamine (10) prepared according to Example 9B of the present invention (compound A) and according to Russian patent No. 2144538 by Ponomarev (compound B), OV2774 cells (seeding density: 50–75 cells/mm$^2$ in RPMI-1640 w. P. (with phenol red), 5% fetal calf serum, 2 mM Glutamax I, 100, g/mL Penicillin/Streptomycin) were incubated with increasing concentrations of up to 50 μM for 24 hours. Cell survival was measured after an additional 24 hours in sensitizer-free medium using the neutral red assay. Values are expressed as a percentage of the non-incubated control samples. For each incubation concentration, three independent experiments were performed in quadruplicates. Data from the experiments are listed in FIG. 1. Compound A showed a lower cytotoxicity towards OV2774 cells as compared with compound B. Cell survival was not significantly decreased for incubation concentrations up to 25 μM (compound B: 10 μM). So far, the IC$_{50}$ value (incubation concentration, which decreases cell growth to 50% as compared with controls) could not be determined. The highest tested incubation concentration resulted in a cell survival of greater 80%.

Example 32

Determination of Phototoxicity in OV2774 Cells, Under Irradiation at 670 nm, of Water-soluble Salt of Chlorin e$_6$ (7) with N-methyl-D-glucamine (10) Prepared According to the Present Invention Versus that Produced According to Ponomarev (RU2144538)

To determine phototoxicity of water-soluble salt of chlorin e$_6$ (7) with N-methyl-D-glucamine (10) prepared according to Example 9 of the present invention (compound A) and according to Russian Patent No. 2144538 by Ponomarev (compound B), OV2774 cells (seeding density: 50–75 cells/mm$^2$ in RPMI-1640 w/o P. (with phenol red), 5% fetal calf serum, 2 mM Glutamax I, 100 μg/mL Penicillin/Streptomycin) were incubated with the same concentration used in the previous experiments with compound B (10 μM, 24 h). Illumination was performed at 670 nm (10–25 mW/cm$^2$, 0.1–2.5 J/cm$^2$) after a second incubation period in medium without photosensitizers and without phenol red. Cell survival was measured using the neutral red assay. Values are expressed as a percentage of incubated, but non-illuminated controls. Five independent experiments were performed in quadruplicates. ID$_{50}$ values (fluence (energy density), which decreases cell growth to 50% as compared with controls) of the samples served as a quantitative measure of phototoxicity. Data from the experiments are given in FIG. 2. Results showed a somewhat higher phototoxicity of compound A as compared with compound B. The ID$_{50}$ value was about half that of compound B (0.1 J/cm$^2$ vs. 0.2 J/cm$^2$).

Example 33

Determination of Dark Toxicity (Cytotoxicity) of Water-soluble Salts of Chlorin (7) and Pheophorbide [(4), (22) and (25)] Derivatives with N-methyl-D-glucamine (10) in HeLa Cells To determine dark toxicity of the water-soluble salts of chlorin e$_6$ (7) and pheophorbide-a derivatives (4, 22,25) with N-methyl-D-glucamine (10) prepared according to Examples 9, 17, 19, and 21, HeLa (human cervix carcinoma cells) cell monolayer cultures were incubated in 96-well plates (seeding density: 7 000 cells per well in Dulbeco-modified essentional medium (DMEM) with 10% fetal calf serum) with increasing concentrations of photosensitizer in the amount from 2 to 500 μg/mL and incubated for 48 hours.

The cells were washed with pure DMEM and treated with 10% formalin for 15 minutes at room temperature. The cells were twice washed with water, incubated for 15 minutes with 0.1% solution of crystal violet (50 μl/well), then washed with water and treated with ethanol (100 μl/well). Optical densities of ethanol solutions formed were determined with Specord 100 (Analytik Jena AG, Germany) spectrophotometer at 594 nm to monitor cell survival.

Values are expressed as percentages of non-incubated controls. For each incubation concentration eight experiments were performed. Data from the experiments are given in Table 1, which shows the $IC_{50}$ and $IC_{80}$ values (incubation concentrations, which decrease cell growth up to 50% and 20% as compared with controls)

TABLE 1

Dark toxicity (cytotoxicity) data for water-soluble salts of chlorin (7) and pheophorbide [(4), (22) and (25)] derivatives with N-methyl-D-glucamine (10) in HeLa cells (Example 33)

| Parent acid component | $IC_{50}$ (μg/mL) | $IC_{80}$ (μg/mL) |
| --- | --- | --- |
| (4) | 20 | 100 |
| (7) | 150 | 200 |
| (22) | 300 | 400 |
| (25) | * | * |

* Could not be determined (>1000 μg/mL).

Example 34

Determination of Phototoxicity of Water-soluble Salt of Chlorin (7) and Pheophorbide [(4), (22) and (25)] Derivatives with N-methyl-D-glucamine (10) in HeLa Cells Under Irradiation at 662 nm.

To determine phototoxicity of the water-soluble salts of chlorin $e_6$ (7) and pheophorbide-a (4, 22, 25) derivatives with N-methyl-D-glucamine (10) prepared according to Examples 9, 17, 19 and 21, HeLa (human cervix carcinoma cells) cell monolayer cultures were incubated in 96-well plates (seeding density: 30,000 cells per well in DMEM with 10% fetal bovine serum) with increasing concentrations of photosensitizer in the amount from 0.01 to 40 μg/mL. Illumination was performed at 662 nm [Ceralas PDT laser, BioLitec AG, Germany; 150 mW/cm², 5–20 J/cm²) after a 30-minute incubation period. Cell survival was measured using the MTT assay. Values are expressed as percentages of illuminated, but non-incubated controls. Experiments were performed in octuplets. Data from the experiments are given in Table 2, which shows $IC_{50}$ and $IC_{90}$ values observed after 10 J/cm² irradiation.

TABLE 2

Phototoxicity data for water-soluble salts of chlorin (7) and pheophorbide [(4), (22) and (25)] derivatives with N-methyl-D-glucamine (10) in HeLa cells (Example 34)

| Parent acid component | $IC_{50}$ (μg/mL) | $IC_{90}$ (μg/mL) |
| --- | --- | --- |
| (4) | 8.0 | 22.0 |
| (7) | 3.0 | 9.0 |
| (22) | 1.25 | 5.0 |
| (25) | 0.05 | 0.17 |

Example 35

Determination of Phototoxicity of Water-soluble Salts of Chlorin (7) and Pheophorbide [(4), (22) and (25)] Derivatives with N-methyl-D-glucamine (10) in Anti-microbial Photodynamic Therapy Experiments The microorganisms used were museum and clinical strains of Staphylococcus aureus (ATCC25923), Enterococcus faecalis (ATCC29212) and Candida spp (clinical).

Bacterial colonies were cultivated on the following solid media types: Staphylococcus aureus on staphylococcus agar 110, Enterococcus faecalis on base of Columbia agar with 5% horse blood, Candida spp on Saburo dextrose agar.

Initial bacterial suspension (IBS) in isotonic NaCl solution was prepared according to McFarland standard with the value of 0.5–1.0 (1.5–5×10⁸ bacterial cells in 1 mL) followed by 1:100 dilution.

For proper control of bacterial cell count a portion of IBS was diluted 1:1000 with isotonic NaCl solution (until 10⁻³ of initial concentration), and three aliquots of 0.1 mL were taken and planted each on a separate Petri dish with media appropriate for the microorganisms. Bacterial colonies were incubated during 24 hours (48 hours for Staphylococcus aureus) at 37° C., then colonies were counted and an average value of each of the 3 Petri dishes was used as control figure.

A). Control of temperature and laser irradiation actions.

2.0 mL of initial bacterial suspension (IBS) was stored at 37° C. for 30 min and then diluted to 1:1000 with isotonic NaCl solution (until 10-3 of initial concentration) and three aliquots of 0.1 mL were taken and planted each on separate Petri dish with media appropriate for the microorganisms. Bacterial colonies were kept during 24 hours at 37° C., then counted and an average value of each of 3 Petri dishes was determined and used as the control value.

Another sample of IBS (2.0 mL) was stored at 37° C. for 30 minutes then irradiated with laser light in 40 mm Petri dish (thickness of suspension layer—2 mm) with "Ceralas PDT" laser with an output power of 3 W for 210 seconds, so that the dose of delivered light energy is of 50 J/cm². The mixture was diluted to 1:1000 with isotonic NaCl solution (until 10⁻³ of initial concentration), and three aliquots of 0.1 mL were taken and planted each on a separate Petri dish, cultivated and then counted as described above.

The data of Table 3 [treatment regimes B and C presented for (7)] show that the storage of IBS at 37° C. for 30 minutes without photosensitizer and under laser irradiation with the dose of 50 J/cm² does not practically affect bacterial viability.

B). Dark toxicity determination.

0.5 mL of a stock solution of photosensitizer with a concentration of 500 pg/mL was added to 2.0 mL of IBS to make a resulting concentration of photosensitizer of 100 μg/mL. The suspension formed was stored at 37° C. for 30 minutes, then diluted to 1:1000 with isotonic NaCl solution (until 10⁻³ of initial concentration). 3 portions of 0.1 mL were taken and planted on 3 Petri dishes and then counted as described above.

The data of Table 3 show that the photosensitizers of the present invention have no practical dark toxicity effect under a concentration of 100 μg/mL within a 30 minute incubation.

C). Phototoxicity determination.

0.125 or 0.5 mL of a stock solution of photosensitizer with concentration of 500 μg/mL were added to 2.0 mL portions of IBS to make resulting concentrations of photosensitizer of 25 and 100 μg/mL, respectively. The suspensions formed were stored at 37° C. for 30 minutes, then irradiated with a density of 50 J/cm². Three 0.1 mL aliquots were taken and planted on 3 Petri dishes. Parts of remaining suspensions were diluted to 1:100 or 1:1000 with isotonic NaCl solution (until $10^{-2}$ or $10^{-3}$ of initial concentration), and 3 aliquots of 0.1 mL from each dilution were planted on 3 Petri dishes and then counted as described above.

The data of Table 3 illustrates the potential applicability of the water-soluble salts of present invention as photosensitizers for anti-microbial photodynamic therapy.

TABLE 3

Application of water-soluble salts of chlorin (7) and pheophorbide [(4), (22) and (25)] derivatives with N-methyl-D-glucamine (10) in anti-microbial photodynamic therapy experiments (Example 35)

| Experimental conditions | | Bacterial Counts | | |
|---|---|---|---|---|
| Parent acid component | Treatment regime* | *Enterococcus faecalis* (ATCC29212) | *Staphylococcus aureus* ATCC25923 | Candida spp |
| (7) | A | $3.9 \times 10^6$ | $0.11 \times 10^6$ | $2.7 \times 10^6$ |
| | B | $3.5 \times 10^6$ | $0.11 \times 10^6$ | $1.5 \times 10^6$ |
| | C | $4.4 \times 10^6$ | $0.11 \times 10^6$ | $1.1 \times 10^6$ |
| | D | $1.3 \times 10^6$ | $0.12 \times 10^6$ | $1.3 \times 10^6$ |
| | E | 0 | $2.8 \times 10^2$ | 0 |
| | F | 0 | $2.2 \times 10^2$ | 0 |
| (4) | A | $0.96 \times 10^6$ | $1.78 \times 10^6$ | |
| | D | $0.92 \times 10^6$ | $1.46 \times 10^6$ | |
| | E | $2.46 \times 10^3$ | 0 | |
| | F | $2.44 \times 10^3$ | 0 | |
| (22) | A | $0.96 \times 10^6$ | $1.78 \times 10^6$ | |
| | D | $0.92 \times 10^6$ | $1.46 \times 10^6$ | |
| | E | $0.04 \times 10^2$ | $1.2 \times 10^2$ | |
| | F | $0.2 \times 10^2$ | $0.12 \times 10^2$ | |
| (25) | A | $2.25 \times 10^6$ | $1.52 \times 10^6$ | |
| | D | $1.6 \times 10^6$ | $1.3 \times 10^6$ | |
| | E | 0 | 0 | |
| | F | 0 | 0 | |

*Treatment regimes:
A, control bacterial count in the initial bacterial suspension (IBS) used;
B, bacterial count after IBS thermostating at 37° C. for 30 minutes;
C, bacterial count after laser irradiation with the dose of 50 J/cm² (Ceralas PDT, 3 W, 210 seconds);
D, bacterial count after 30 minute incubation with photosensitizer (concentration of 100 μg/mL);
E, bacterial count after photodynamic treatment with the concentration of photosensitizer of 25 μg/mL;
F, bacterial count after photodynamic treatment with the concentration of photosensitizer of 100 μg/mL;

Having described preferred embodiments of the invention with reference to the examples, it is to be understood that the invention is not limited to the precise embodiments, and that various changes and modifications may be effected therein by skilled in the art without departing from the scope or spirit of the invention as defined in the appended claims.

What is claimed is:

1. A method to prepare pharmaceutical-grade water-soluble porphyrin salts with hydrophilic amines, comprising the steps of:

a) one or two step direct acidic alcoholysis of biological raw material giving crystalline alkyl pheophorbide;

b) conversion of the obtained alkyl pheophorbide into an acidic porphyrin; and c) reaction of the acidic porphyrin with a hydrophilic organic amine in a medium selected from a group consisting of water and an aqueous organic solution.

2. A method according to claim 1, wherein said biological raw material is selected from the group, comprising naturally occurring plants, algae, blood components, insect excretions, microorganisms.

3. A method according to claim 2, wherein naturally occurring plants and algae comprise *Spirulinaplatensis, Spirulina maxima, Chiorella*, nettle and spinach.

4. A method according to claim 1, wherein direct one or two step acidic alcoholysis is selected from a group consisting of methanolysis and ethanolysis.

5. A method according to claim 1, wherein said hydrophilic organic amine is selected from the group consisting of N-methyl-D-glucamine, amino alkyl glycosides, tris (hydroxymethyl)aminomethane (TRIS), and derivatives thereof, aminoacids and oligopeptides.

6. A method according to claim 5, wherein said organic amine is N-methyl-D-glucamine.

7. A method to prepare pharmaceutical-grade water-soluble porphyrin salts with hydrophilic amines, comprising reaction of an acidic porphyrin with a hydrophylic organic amine in a medium selected from a group consisting of water and an aqueous organic solution.

8. A method according to claim 7, wherein said hydrophilic organic amine is selected from the group consisting of N-methyl-D-glucamine, amino alkyl glycosides, tris (hydroxymethyl)aminomethane (TRIS), and derivatives thereof, aminoacids and oligopeptides.

9. A method according to claim 7, wherein said organic amine is N-methyl-D-glucamine.

10. A method to prepare pharmaceutical-grade water-soluble porphyrin salts with hydrophilic amines, comprising the steps of:

a) one or two step direct acidic alcoholysis of biological raw material giving crystalline alkyl pheophorbide;

b) conversion of the obtained alkyl pheophorbide into an acidic porphyrin;

c) reaction of the acidic porphyrin with a hydrophilic organic amine in a medium selected from a group consisting of water and an aqueous organic solution; and d) purification of a water-soluble porphyrin salt with hydrophilic amine by reversed phase chromatography with the use of suitable solvents.

11. A method according to claim 10, wherein said biological raw material is selected from the group consisting of naturally occurring plants, algae, blood components, insect excretions, and microorganisms.

12. A method according to claim 11, wherein naturally occurring plants and algae comprise *Spirulinaplatensis, Spirulina maxima, Chiorella*, nettle and spinach.

13. A method according to claim 10, wherein direct one or two step acidic alcoholysis is selected from a group consisting of methanolysis and ethanolysis.

14. A method according to claim 10, wherein said hydrophilic organic amine is selected from a group consisting of N-methyl-D-glucamine, aminoalkyl glycosides, TRIS and derivatives thereof, aminoacids and oligopeptides.

15. A method according to claim 14, wherein said organic amine is N-methyl-D-glucamine.

16. A method to prepare pharmaceutical-grade water-soluble porphyrin salts with hydrophilic amines, comprising a) reaction of an acidic porphyrin with a hydrophylic organic amine in a medium chosen from the group consisting of water and an aqueous organic solution; and b) purification of a water-soluble porphyrin salt with hydrophilic amines by reversed phase chromatography with the use of suitable solvents.

17. A method according to claim 16, wherein said hydrophilic organic amine is selected from the group consisting of N-methyl-D-glucamine, amino alkyl glycosides, tris(hydroxymethyl)aminomethane TRIS (TRIS), and derivatives thereof, aminoacids and oligopeptides.

18. A method according to claim 17, wherein said organic amine is N-methyl-D-glucamine.

19. Water-soluble porphyrin salts with hydrophilic amines, of a pharmaceutical grade according to GMP standards, of formula 1 or 2:

(1)

(2)

Wherein B is a ring having the structure:

-continued

Wherein:
$R^1$=—CH=CH$_2$, —CH(OAlk)CH$_3$, —CHO, —C(O)CH$_3$, —CH$_2$CH$_3$, —CH(Alk)CH(COAlk)$_2$, —CH$_2$CH(COAlk)$_2$, —CH(Alk)CH$_2$COAlk, CH(Alk)CH$_2$CH(OH)CH$_3$, and —CH$_2$CH$_2$CH(OH)CH$_3$ $R^2$=—CH$_3$, —CHO, —CH(OH)Alk, —CH=CHAlk, CH$_2$OH, and CH$_2$OAlk;

$R^3$=—OH, —OAlk, —NH-Alk, NH—X—COO$^-$(HG)$^+$, —NH—Y—NR$^8$R$^9$, -and NH—Y—OH;

$R^4$=—O$^-$(HG)$^+$, —OAlk, —NH-Alk, and NH—X—COO$^-$(HG)$^+$;

$R^5$=—O$^-$(HG)$^+$, —OAlk, —NH-Alk, and NH—X—COO$^-$(HG)$^+$;

$R^6$=H and —COOAlk;

$R^7$=—O$^-$(HG)$^+$, —OAlk, —NH-Alk, and —NH—X—COO$^-$(HG)$^+$;

$R^8$=H and Alk $R^9$=H and Alk

Wherein:
—NH—X—COO=the residue of organic amino acid;

X=alkylidene, peptides, oligopeptides and —(CH$_2$CH$_2$O)$_n$CH$_2$CH$_2$—, wherein n=1–30;

Y=alkylidene and —(CH$_2$CH$_2$O)$_n$CH$_2$CH$_2$—, wherein n=1–30;

G=a hydrophilic organic amine; and

Alk=an alkyl substituent.

20. The use of said water-soluble porphyrin salts with hydrophilic amines of claim 19 in photodynamic therapy to necrotize hyperproliferative tissue and infections, comprising the steps of:
 a) incorporating said salts into a pharmaceutically acceptable application vehicle;
 b) administering said vehicle to a treatment area;
 c) allowing for sufficient time for said porphyrin salts to preferentially accumulate in diseased tissue in said treatment area; and
 d) irradiating said treatment area with light of an appropriate wavelength and sufficient power to active said porphyrin salts, thereby necrotizing cells of said diseased tissue.

21. A use according to claim 20, wherein said application vehicle is a dermatological cream.

22. A use according to claim 20 comprising the additional initial step of dissolving bis- salts of said salts in water in the presence of an amount of said hydrophilic amine before use, wherein said amount is no greater than 2 mole equivalents to maintain stability of water solubility of said salts during storage.

23. A stable aqueous solution comprising a bis-salt of said pharmaceutical grade water soluble porphyrin salts with hydrophilic amines according to claim 19 and an amount of said hydrophilic amine wherein said amount is no greater than 2 mole equivalents to maintain stability of water solubility of said salts during storage.

24. Pharmaceutical compositions for treatment of cancer and other hyperproliferative diseases, comprising said water-soluble porphyrin salts with hydrophilic amines described in claim 19 as an active ingredient, and a suitable carrier.

25. Water-soluble porphyrin salts with organic amines according to claim 19, produced according to the method in claim 1, claim 7, claim 10 or claim 16.

26. The use of said water-soluble porphyrin salts with organic amines of claim 25 in photodynamic therapy of to necrotize hyperproliferative tissue and infections, comprising the steps of:
 a) incorporating said salts into a pharmaceutically acceptable application vehicle;
 b) administering said water-soluble porphyrin salts to a treatment area;
 c) allowing for sufficient time for said porphyrin salts to preferentially accumulate in diseased tissue in said treatment area;
 d) irradiating said treatment area with light of an appropriate wavelength and sufficient power to activate said porphyrin salts, thereby necrotizing cells of said diseased tissue.

27. A use according to claim 26, wherein said vehicle is a dermatological cream.

28. A use according to claim 26 comprising the additional initial step of dissolving bis- salts of said porphyrin salts in water in the presence of an amount of said hydrophilic amine before use, wherein said amount is no greater than 2 mole equivalents to maintain stability of water solubility of said salts during storage.

29. A use according to claim 22, wherein said amount is between 0.05 and 0.5 mole equivalents of said hydrophilic amine.

30. A use according to claim 23, wherein said amount is between 0.05 and 0.5 mole equivalents of said hydrophilic amine.

31. A use according to claim 28, wherein said amount is between 0.05 and 0.5 mole equivalents of said hydrophilic amine.

* * * * *